United States Patent
Overes et al.

(10) Patent No.: US 8,663,224 B2
(45) Date of Patent: Mar. 4, 2014

(54) SURGICAL NAIL

(75) Inventors: Tom Overes, Langendorf (CH); Bruno Walter, Solothurn (CH); Martin Jaeger, Gundelfingen-Wildtal (DE); Daniel Andermatt, Solothurn (CH)

(73) Assignee: Depuy Synthes Products, LLC, Raynham, MA (US)

( * ) Notice: Subject to any disclaimer, the term of this patent is extended or adjusted under 35 U.S.C. 154(b) by 78 days.

(21) Appl. No.: 13/227,169

(22) Filed: Sep. 7, 2011

(65) Prior Publication Data

US 2012/0226326 A1    Sep. 6, 2012

Related U.S. Application Data

(60) Provisional application No. 61/381,264, filed on Sep. 9, 2010, provisional application No. 61/476,597, filed on Apr. 18, 2011, provisional application No. 61/498,892, filed on Jun. 20, 2011, provisional application No. 61/500,297, filed on Jun. 23, 2011.

(51) Int. Cl.
*A61B 17/56* (2006.01)
*A61B 17/58* (2006.01)
*A61F 2/30* (2006.01)

(52) U.S. Cl.
USPC .................................. 606/62; 606/64; 606/67

(58) Field of Classification Search
USPC ............................................... 606/62, 64, 67
See application file for complete search history.

(56) References Cited

U.S. PATENT DOCUMENTS

| | | | |
|---|---|---|---|
| 2,381,050 A | 8/1945 | Hardinage | |
| 2,998,007 A | 8/1961 | Herzog | |
| 3,143,915 A | 8/1964 | Tendler | |
| 3,143,916 A | 8/1964 | Rice | |
| 3,678,925 A | 7/1972 | Fischer et al. | |
| 4,453,539 A | 6/1984 | Raftopoulos et al. | |
| 4,628,920 A | 12/1986 | Mathys, Jr. et al. | |
| 4,653,487 A * | 3/1987 | Maale ............................. | 606/62 |
| 4,854,312 A | 8/1989 | Raftopoulos et al. | |
| 4,862,883 A | 9/1989 | Freeland | |
| 4,875,474 A | 10/1989 | Border | |
| 5,057,103 A | 10/1991 | Davis | |

(Continued)

FOREIGN PATENT DOCUMENTS

| CN | 201131789 | 10/2008 |
|---|---|---|
| CN | 101474092 | 7/2009 |

(Continued)

OTHER PUBLICATIONS

CarboFix Orthopedic Ltd., Expendable Implants Technology, 4 sheets.

*Primary Examiner* — Andrew Yang
(74) *Attorney, Agent, or Firm* — Fay Kaplun & Marcin, LLP

(57) ABSTRACT

A surgical nail for treating a fractured bone includes a nail body extending along a longitudinal axis from a trailing end to a leading end and including a trailing end locking aperture extending transversely through a trailing end portion thereof and a leading end locking aperture extending transversely through a leading end portion thereof; a trailing end connecting element located at the trailing end of the nail body adapted and configured to be coupled to a trailing end aiming guide; and a leading end connecting element at the leading end of the nail body adapted and configured to be coupled to a leading end aiming guide.

22 Claims, 29 Drawing Sheets

(56) References Cited

U.S. PATENT DOCUMENTS

| | | |
|---|---|---|
| 5,102,413 A | 4/1992 | Poddar |
| 5,116,335 A | 5/1992 | Hannon et al. |
| 5,281,225 A | 1/1994 | Vicenzi |
| 5,474,561 A | 12/1995 | Yao |
| 5,540,688 A | 7/1996 | Navas |
| 5,658,310 A | 8/1997 | Berger |
| 5,685,826 A | 11/1997 | Bonutti |
| 5,695,515 A | 12/1997 | Orejola |
| 6,454,810 B1 | 9/2002 | Lob |
| 6,551,321 B1 | 4/2003 | Burkinshaw et al. |
| 6,558,388 B1 | 5/2003 | Bartsch et al. |
| 6,575,973 B1 | 6/2003 | Shekalim |
| 7,135,022 B2 | 11/2006 | Kosashvili et al. |
| 7,722,611 B2 | 5/2010 | Cavallazzi et al. |
| 7,846,162 B2 | 12/2010 | Nelson et al. |
| 7,909,825 B2 | 3/2011 | Saravia et al. |
| 2002/0161369 A1 | 10/2002 | Bramlet et al. |
| 2003/0073999 A1 | 4/2003 | Putnam |
| 2005/0096656 A1 | 5/2005 | Behrens |
| 2006/0064094 A1 | 3/2006 | Levy et al. |
| 2006/0142764 A1 | 6/2006 | Zielsdorf |
| 2008/0161805 A1 | 7/2008 | Saravia et al. |
| 2008/0221574 A1 | 9/2008 | Cavallazzi et al. |
| 2008/0269776 A1 | 10/2008 | Justin et al. |
| 2009/0287213 A1 | 11/2009 | Pieske |

FOREIGN PATENT DOCUMENTS

| | | |
|---|---|---|
| EP | 0738502 | 2/1997 |
| EP | 0777447 | 2/2001 |
| EP | 1227765 | 5/2005 |
| EP | 1759643 | 7/2007 |
| FR | 2741256 | 5/1997 |
| GB | 1 402 557 | 8/1972 |
| GB | 2268068 | 1/1994 |
| JP | 2000166938 | 6/2000 |
| WO | 97/01990 | 1/1997 |
| WO | 98/24380 | 6/1998 |
| WO | 98/36699 | 8/1998 |
| WO | 98/38918 | 9/1998 |
| WO | 01/56487 | 8/2001 |
| WO | 2005/084566 | 9/2005 |
| WO | 2006/090361 | 8/2006 |
| WO | 2008/134287 | 11/2008 |
| WO | 2009/045751 | 4/2009 |
| WO | 2009/155715 | 12/2009 |
| WO | 2010/045116 | 4/2010 |
| WO | 2010/091242 | 8/2010 |
| WO | 2010/093911 | 8/2010 |
| WO | 2010/134078 | 11/2010 |

* cited by examiner

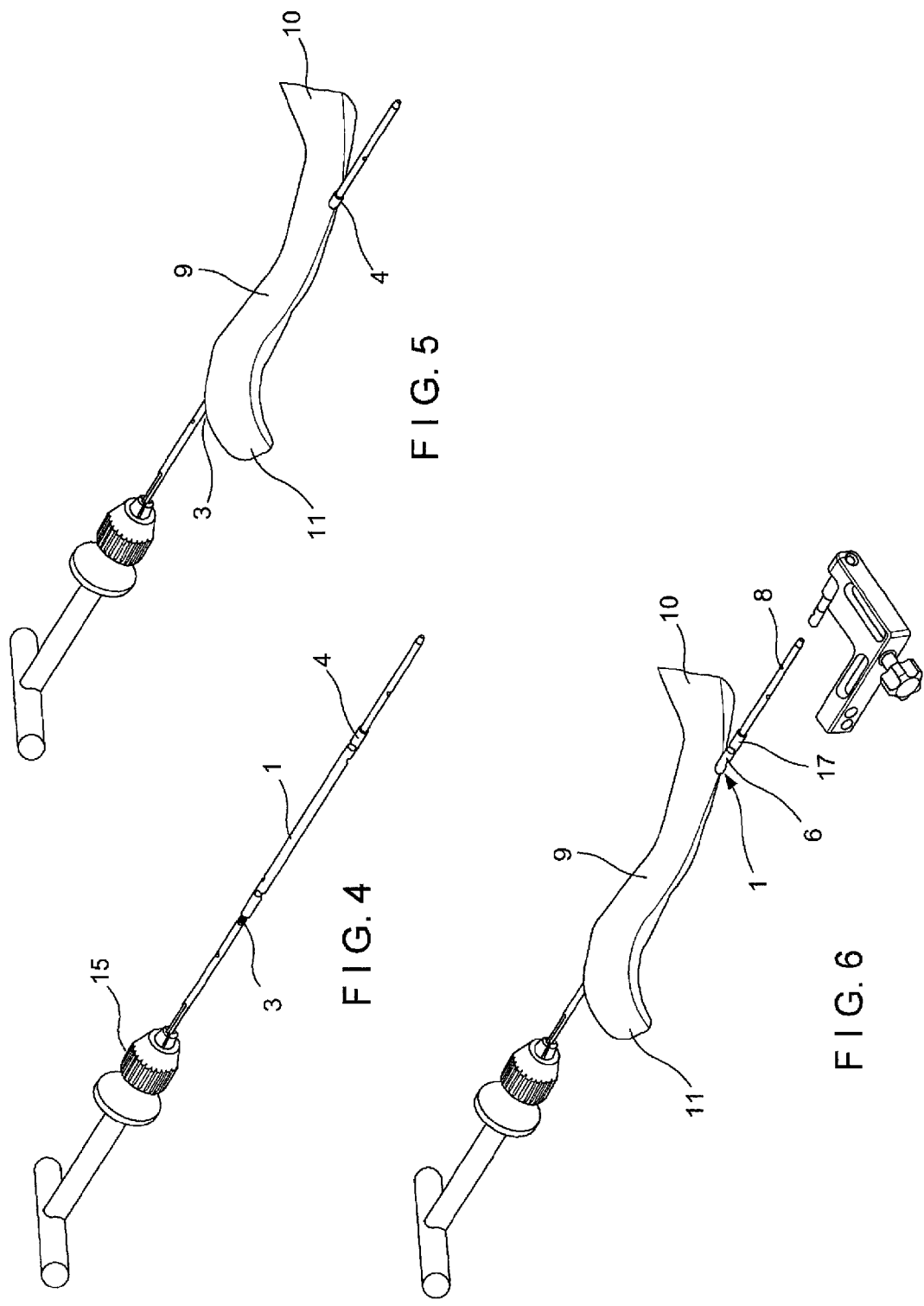

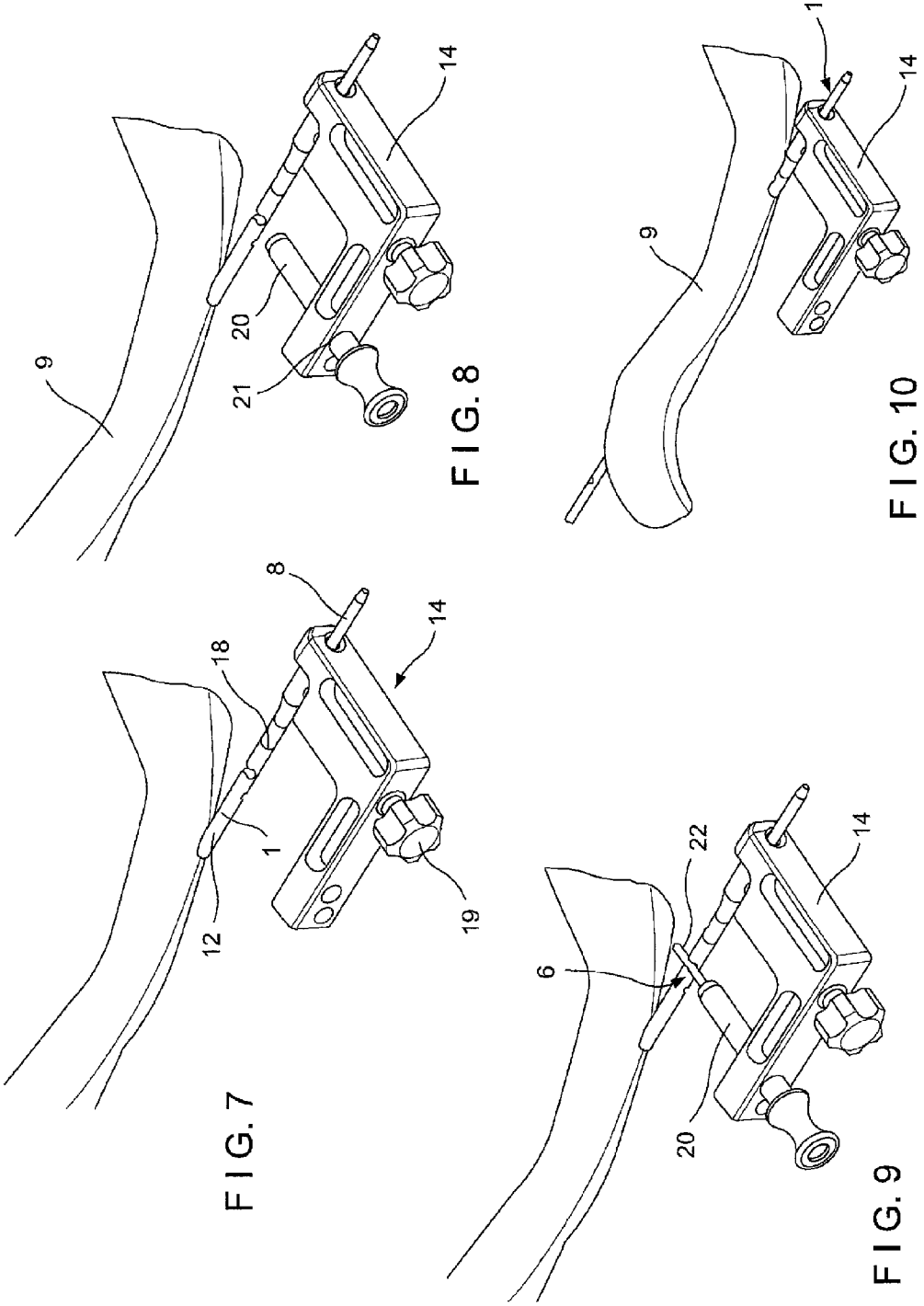

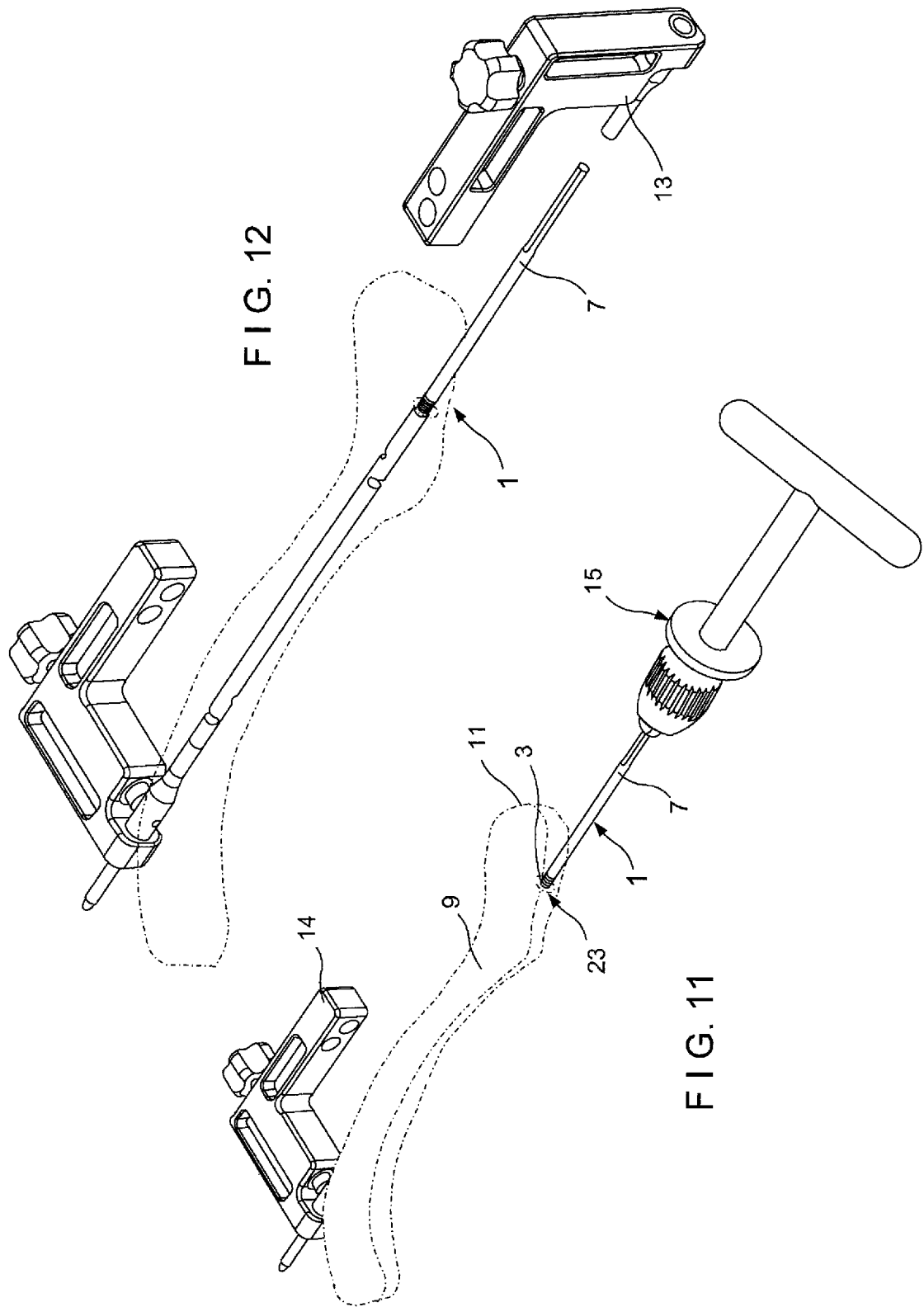

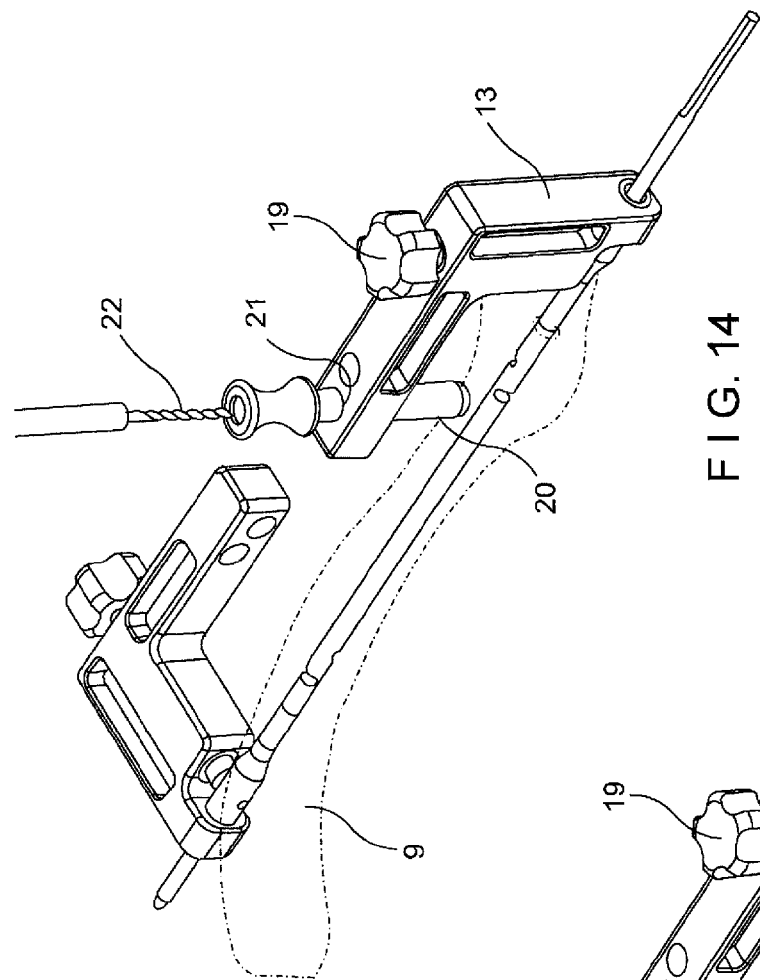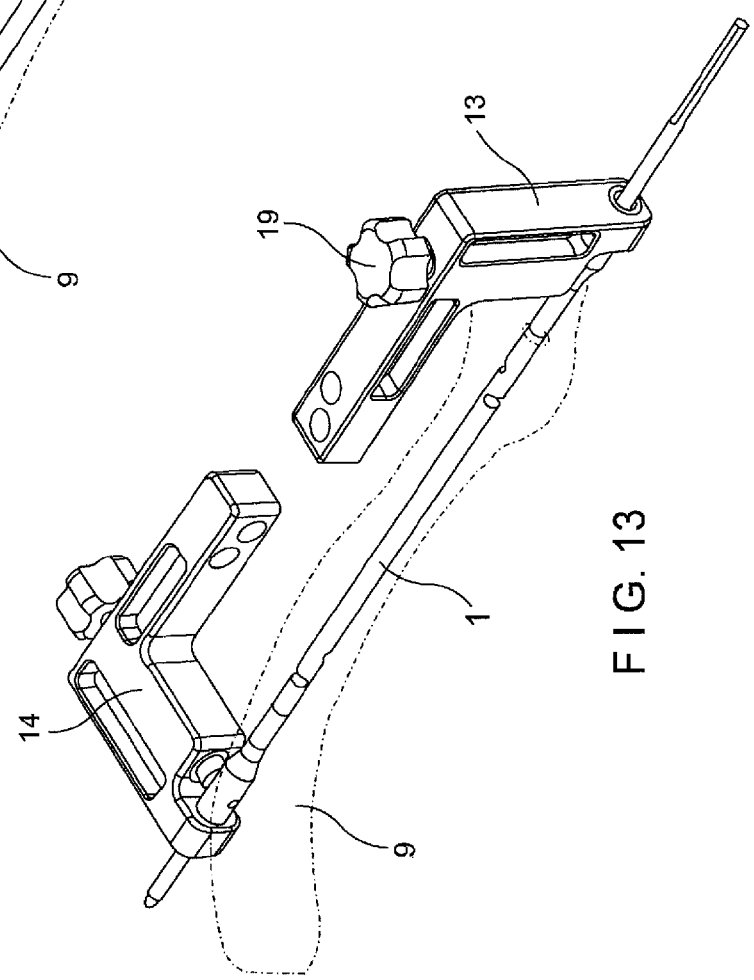

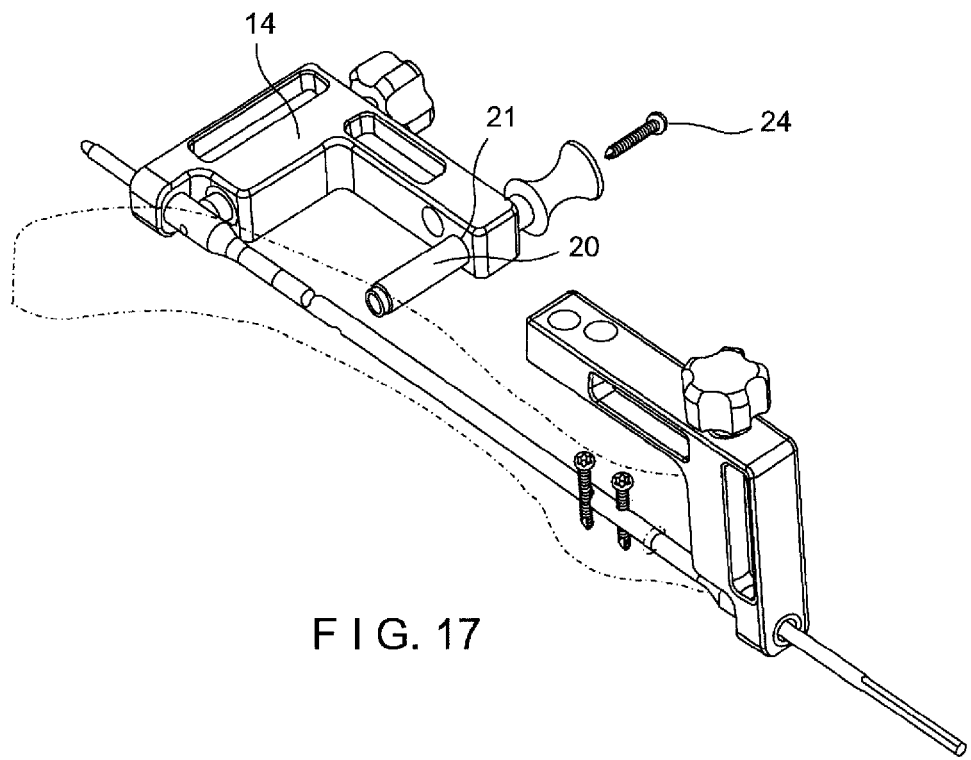
F I G. 17
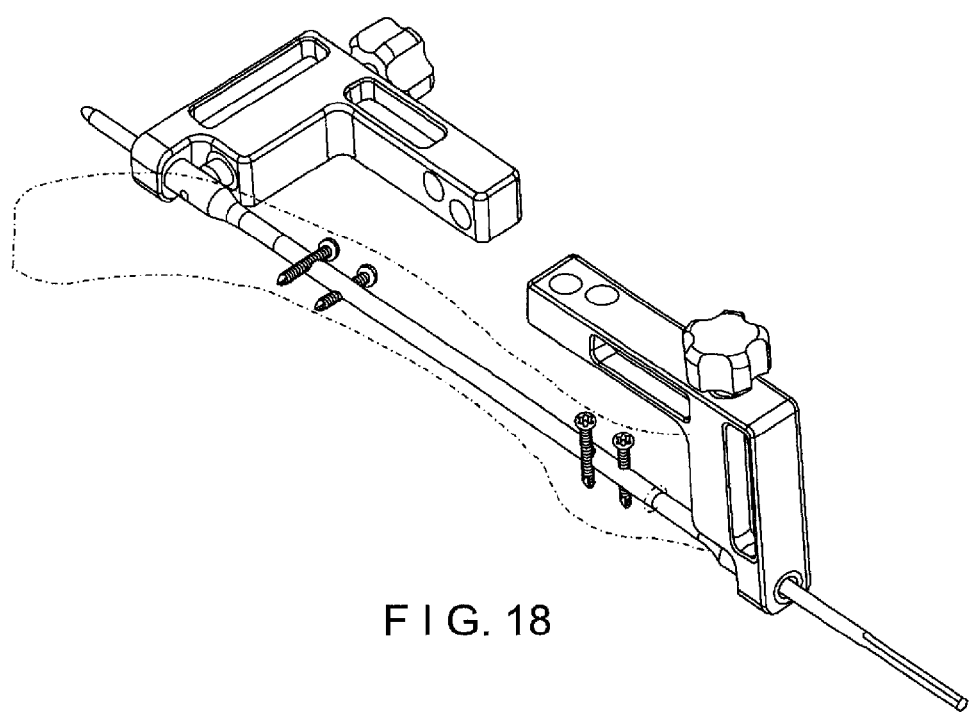
F I G. 18

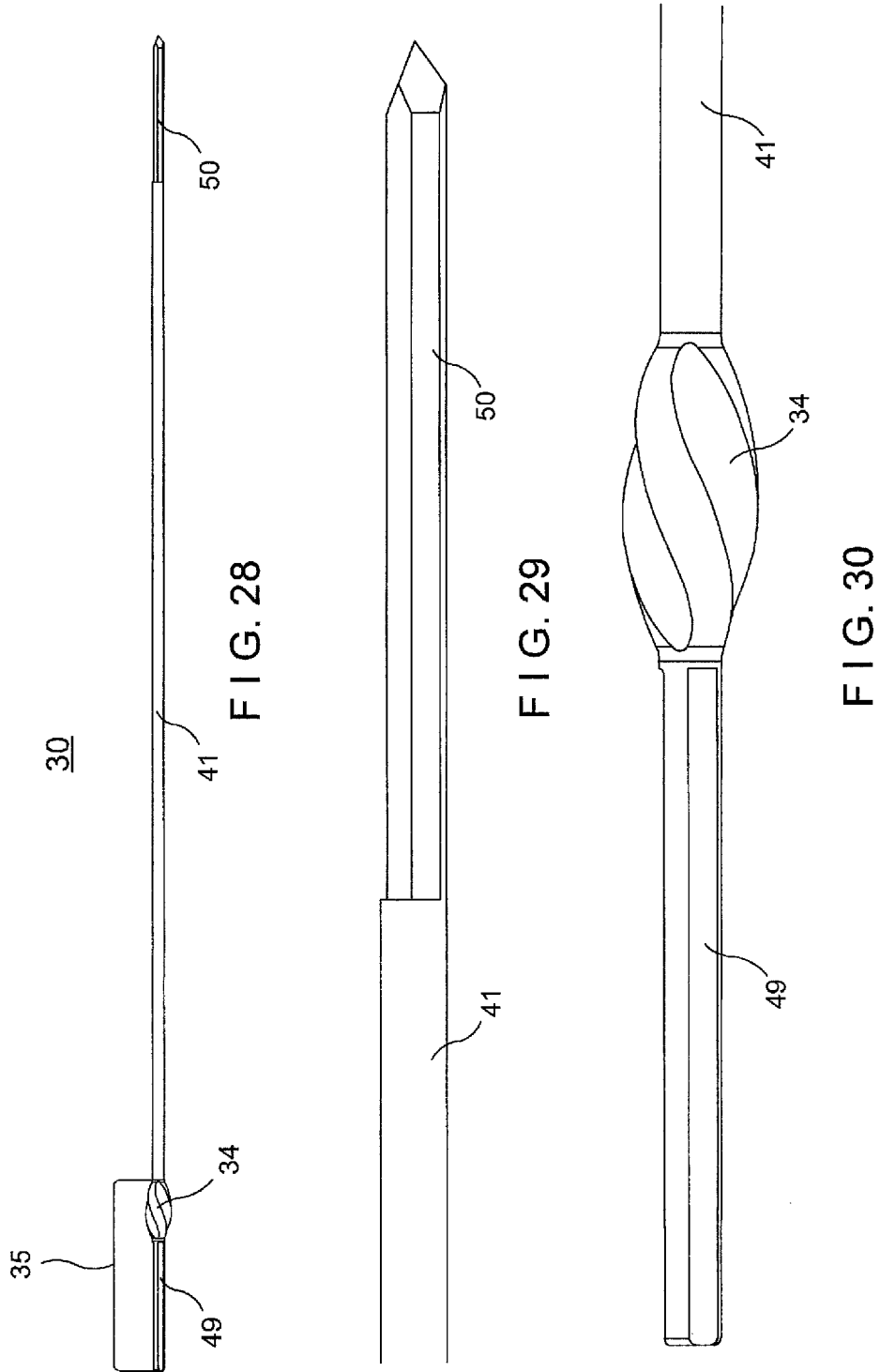

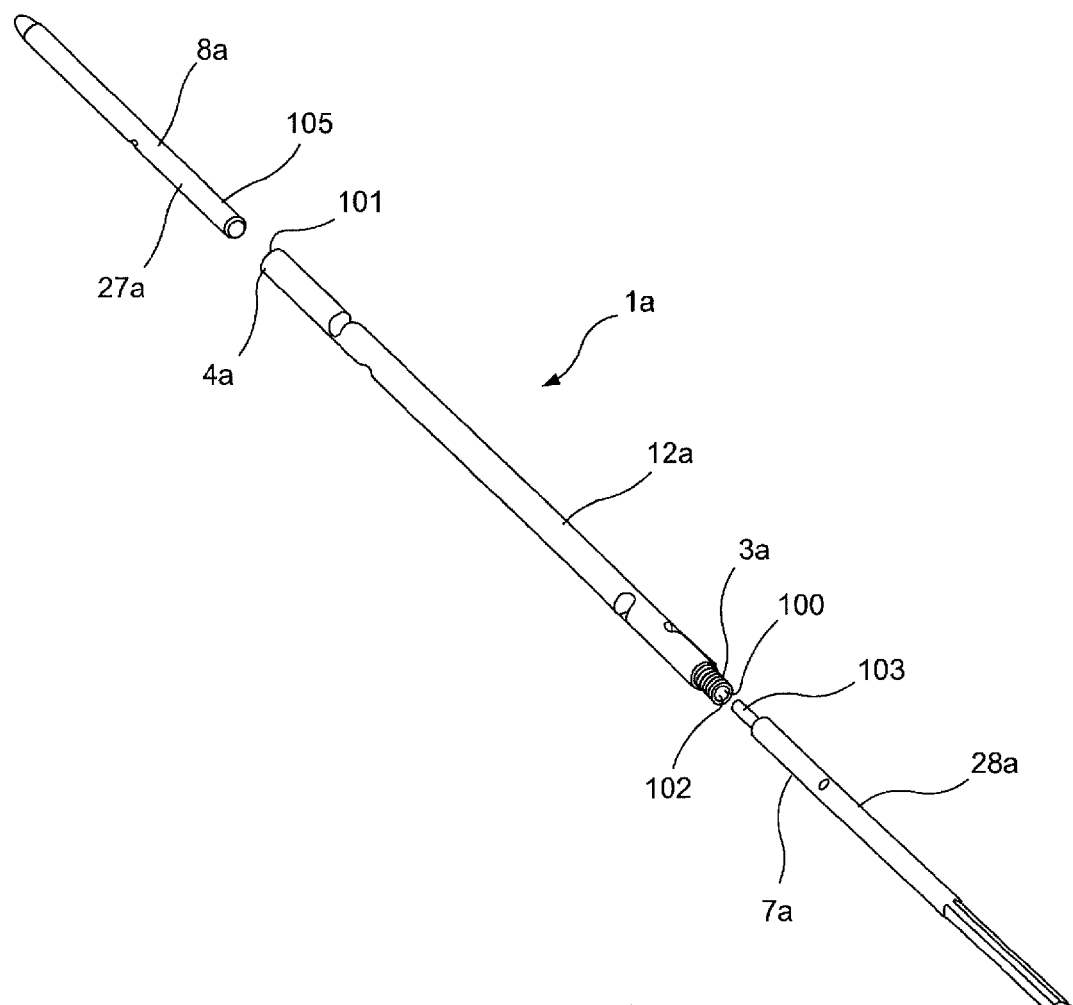
F I G. 35

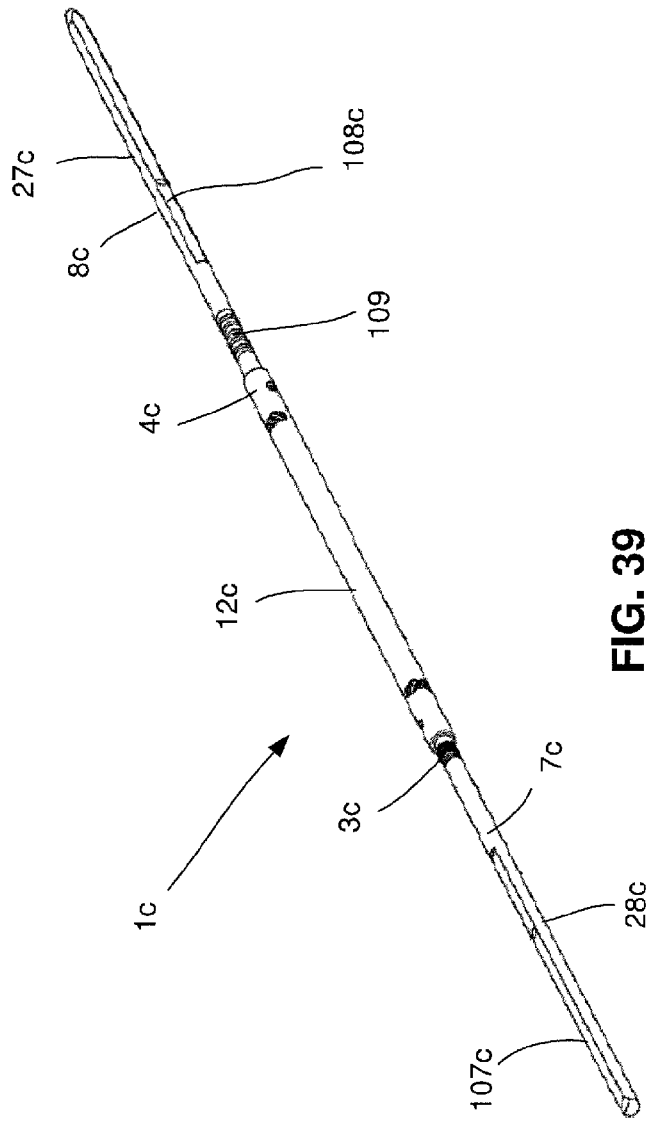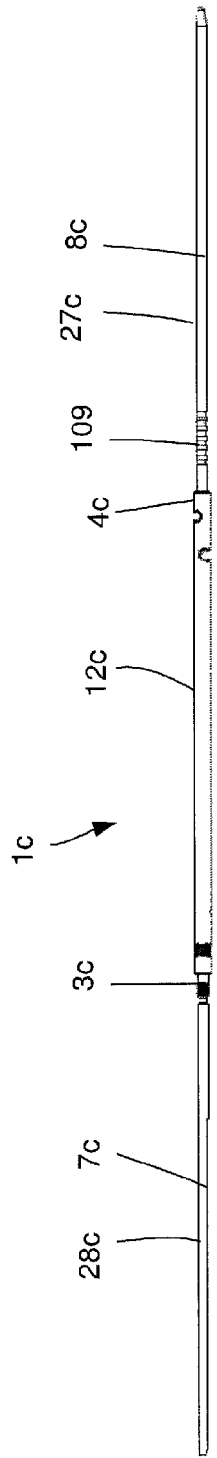
FIG. 39
FIG. 40

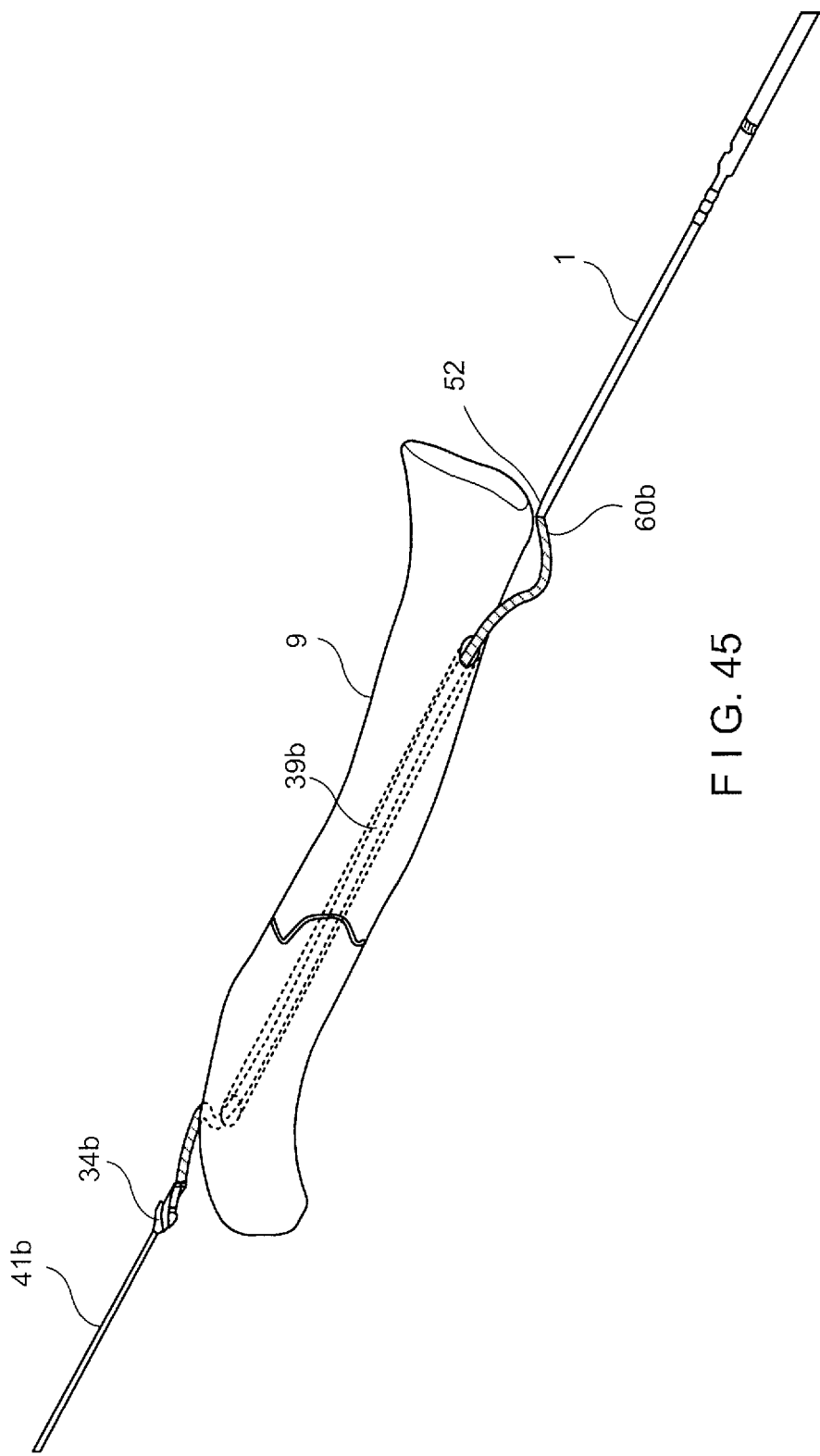
F I G. 45

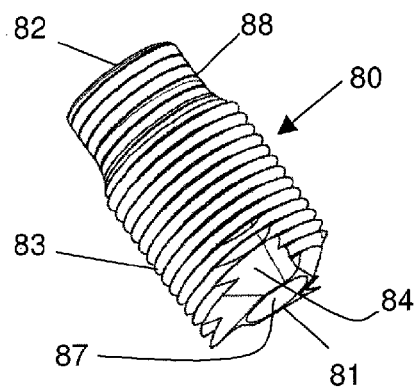
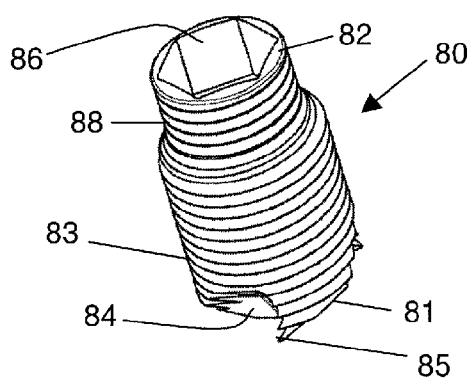
FIG. 52　　　　　　　　　FIG. 53
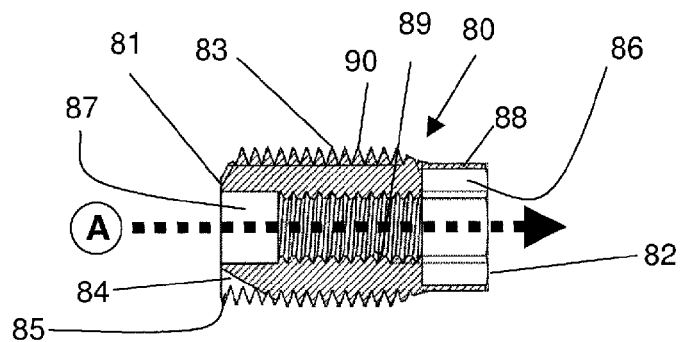
FIG. 54
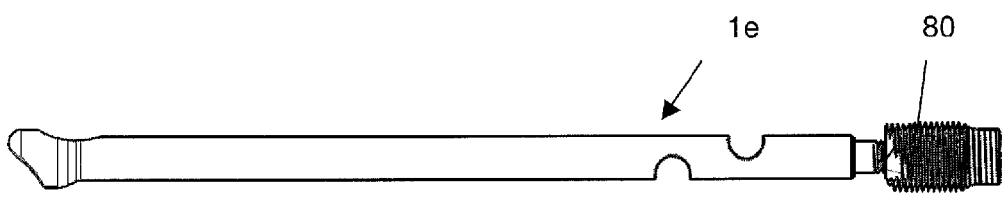
FIG. 55
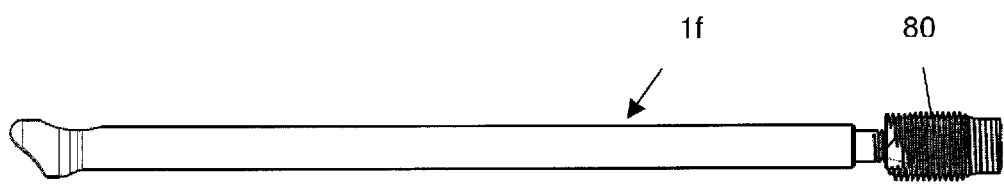
FIG. 56

SURGICAL NAIL

PRIORITY CLAIM

This application claims priority to U.S. Provisional Application Ser. No. 61/381,264 filed on Sep. 9, 2010 and entitled "Surgical Nail," U.S. Provisional Application Ser. No. 61/476,597 filed on Apr. 18, 2011 and entitled "Locking Clavicle Nail" and U.S. Provisional Application Ser. No. 61/498,892 filed on Jun. 20, 2011 and entitled "Surgical Nail" and U.S. Provisional Application Ser. No. 61/500,297 filed on Jun. 23, 2011 and entitled "Clavicle Nail with Lateral Expanding and Actuated Portion," the entire disclosures of which are incorporated herein by reference.

FIELD OF THE INVENTION

The present invention generally relates to a surgical nail and, in particular, to a clavicle nail comprising proximal and distal connecting elements for coupling an aiming guide to a nail body.

BACKGROUND

Clavicle (e.g., collarbone) fractures account for 5 to 7% of adult fractures of which 80 to 85% are in the mid third of the clavicle. Due to the critical structures surrounding the clavicle, the thin medullary canal and the limited bone stock of the clavicle, these fractures may be difficult to treat. Clavicle fractures may be treated with a surgical nail inserted through the bone to fix fractured portions of the bone relative to one another. Locking screws may be inserted through portions thereof to fix the surgical nail therein. In some cases, however, it may be difficult to accurately determine the position of a locking hole in a nail.

SUMMARY OF THE INVENTION

The present invention relates to a surgical nail that allows a user to verify an alignment of guide bores of a distal aiming arm attached to a distal end of a surgical nail upon insertion of the surgical nail into a bone and to correct the alignment if necessary.

The present invention relates to a surgical nail, particularly a clavicle nail and comprises a nail body extending along a longitudinal axis from a proximal end to a distal end and including one or more proximal locking apertures and one or more distal locking apertures. In addition, the surgical nail comprises a proximal rod of having a length $L_C$ and extending proximally from the proximal end of the nail body substantially coaxially with the longitudinal axis, the proximal rod being adapted for coupling a proximal aiming guide to the surgical nail. The proximal rod may have a circular or polygonal cross section. Further, the surgical nail may also comprise a distal rod extending distally from the distal end of the nail body substantially coaxially from the distal end of the nail body. The distal rod may have a circular or polygonal, e.g. hexagonal cross-section. Alternatively, the distal end of the nail body may be configured as a cavity extending into the nail body, wherein the cavity may be provided with an internal thread or the cavity may be configured as a bayonet socket.

Some advantages of the surgical nail according to an exemplary embodiment of the present invention including a proximal rod extending substantially coaxially from the proximal end of the nail body are that the proximal rod permits a proximal aiming guide to be coupled to the nail body and the nail body may be inserted into the bone as far until one or more distal locking apertures protrude from the distal opening of the through hole in the bone so that the position and alignment of the guide bore of a distal aiming arm attached to the nail can be verified by e.g. inserting a drill bit into the guide bore of the distal aiming arm and into the corresponding distal locking aperture in the nail body. Thus, if necessary, the alignment of the distal aiming arm can be corrected.

In one exemplary embodiment of the surgical nail, the proximal rod has a cross-sectional area that is no larger than a cross-sectional area of the nail body. The nail body may have a maximum diameter D while the proximal rod may have a maximum diameter d<D. This configuration of the proximal rod has the advantage that the proximal rod can be pushed into the hole in the bone which has been produced before or during insertion of the surgical nail into the bone so that the surgical nail can be inserted into the bone as far as the distal locking apertures protrude from the bone and the alignment of the guide bores in the distal aiming arm with the distal locking apertures can be verified. Preferably, the proximal rod is integral with the nail body.

In a further exemplary embodiment of the surgical nail, the one or more distal locking apertures are located within a distal portion of the nail body, wherein the distal portion of the nail body has a length $L_D$ measured from the distal end of the nail body and wherein the proximal rod extends from the proximal end of the nail body over a length $L_C$ which is equal to or longer than $L_D$. Thus, the surgical nail may be inserted into the bone so that the distal locking apertures extend distally beyond the distal surface of the bone so that the alignment of the guide bores in a distal aiming guide with the distal locking apertures in the surgical nail can be visually verified. Furthermore, the one or more proximal locking apertures are located within a proximal portion of the nail body, wherein the proximal portion of the nail body has a length $L_P$ measured from the proximal end of the nail body. The length $L_P$ may be equal to or different from the length $L_D$.

In another exemplary embodiment of the surgical nail, the ratio of $L_C$ to $L_D$ is a minimum value of 1.0, but more preferably a minimum value of 3.0. A typical value for the ratio of $L_C$ to $L_D$ may be approximately 4. The length $L_D$ of the distal portion of the nail body is a maximum of up to approximately 40 mm, but preferably a maximum of approximately 10 mm. The length $L_C$ of the proximal rod is a minimum of approximately 10 mm, but preferably a minimum of approximately 60 mm. Further, the ratio of $L_C$ to $L_D$ has a maximum value of approximately 6.0, but more preferably a maximum of approximately 4.5.

In another exemplary embodiment of the surgical nail, a distal connecting element for coupling a distal aiming guide to the surgical nail is configured as a distal rod extending distally from the distal end of the nail body substantially coaxially with a longitudinal axis thereof. This configuration a distal aiming arm to be attached to the nail by sliding the aiming arm over the distal rod. The distal rod may have a length $L_X$ which is preferably longer than $L_P$ and $L_D$. The length $L_X$ of the distal rod may be equal to or different from the length $L_C$ of the proximal rod. Preferably, the distal rod has a cross-sectional area that is no larger than the cross-sectional area of the nail body. Preferably the nail body has a maximum diameter D and the distal rod has a maximum diameter d≤D.

In again another exemplary embodiment of the surgical nail, the angle at which the one or more distal locking apertures extend may be offset with respect to the proximal locking apertures. Suitably, the angle of offset may be in the range of 10° to 90° with respect to the proximal locking apertures, for example, 10°, 20°, 30°, 40°, 50°, 60°, 70°, 80°, 90°.

Preferably, the angle of offset is 90°. The clavicle nail may be inserted from a medial end of the clavicle as well as from a lateral end of the clavicle, on both the left and the right sides of the patient's body.

In yet a further exemplary embodiment of the surgical nail, the distal locking aperture and the proximal locking aperture may extend substantially along the same plane relative to each other.

In yet another exemplary embodiment of the surgical nail, the nail body is straight.

In still another exemplary embodiment of the surgical nail, the nail body is bent or curved. Suitably, the nail body may be curved in the same plane to be a particular shape, preferably, S-shaped. Alternatively, the nail body may be curved in different planes, preferably, double curved in different planes.

The nail body between the proximal and distal locking apertures may be pre-bent to better accommodate an anatomy of the clavicle. Alternatively, the nail body may be flexible or may be comprised of multiple segments such that the nail may be flexible.

In a further exemplary embodiment of the surgical nail, the nail body may comprise a cross-sectional area that is substantially triangular.

In a further exemplary embodiment of the surgical nail, the nail body may comprise a substantially flattened cross-section. The area of the nail body comprising the flattened cross section may be helical in shape. The helical shape may accommodate more easily the shape of a clavicle bone and may improve insertion of the nail body into the clavicle. The nail body may be bent into the helical shape. Alternatively, or in addition, the nail body may be fabricated with the helical shape.

In a further exemplary embodiment, the nail body may comprise an area with a substantially triangular cross-section and an area with a flattened cross section.

In yet a further exemplary embodiment of the surgical nail, each of the one or more proximal locking apertures and the one or more distal locking apertures have a central axis. The proximal and distal rods may each comprises a notch, preferably configured as a through bore having a bore axis wherein the bore axis of the through bore in the proximal rod is parallel to the central axes of the one or more proximal locking apertures and the bore axis of the through bore in the distal rod is parallel to the central axes of the distal locking apertures such that proximal and distal aiming guides, respectively, may be attached in an aligned configuration relative to the surgical nail. Since the distal locking apertures at an angle of 90° with respect to the proximal locking apertures, the clavicle nail may be used for both medial and lateral insertion into the clavicle, from both the left and the right side of the patient's body.

In a still further exemplary aspect of the present invention, one or each of the proximal connecting element and the distal connecting element is removably coupled to the nail body. Suitably, the proximal connecting element is removably coupled to the nail body and the distal connecting element is integrated with the nail body. The removable coupling may be provided by press-fitting, screwing, using a bayonet-type connection, welding, in particular laser welding, or gluing the connecting element to the nail body. The removable coupling may ensure that no sharp edges result from cutting the proximal and/or distal connecting element and may also minimize the potential for soft tissue irritation. The removably couplable connection elements may comprise different or the same material as the nail body.

In accordance with another exemplary aspect of the present invention, a surgical reamer is provided for producing a hole in a clavicle from one of an antero-medial to a postero-lateral or from the postero-lateral to the antero-medial.

In cases where a medullary canal in the clavicle is too small for the nail, the canal may need to be reamed to have a larger diameter to accommodate the nail. For reaming, a light flexible reamer may be used such that a length of the reamer moved along the medullary canal. In some reamers, a reaming head may have a larger diameter then the reaming shaft. Thus, when pushing the reamer through the canal, the shaft may buckle, compromising an accuracy in directing the reamer. The risk of inaccurate reaming is that the reamer may depart from the canal through a side of the bone, damaging arteries, veins or nerves, or even penetrating the lung. One method of guiding drills or reamers in trauma-surgery is placing K-wires and then over-drilling the hole produced by the K-wire with a hollow reamer or drill. K-wires may be placed accurately in bones because the diameter to length ratio is such that flexibility is sufficient and relatively little buckling takes place. In case of the clavicle bone, a relatively thin canal needs to be reamed, of approximately 3 to 4 mm diameter. A hollow reamer to be guided over a K-wire would require a critical small wall-thickness, especially if the initial flexibility is required.

The reamer according to an exemplary embodiment of the present invention is a K-wire having a reamer head.

The reamer may have a plurality of reamer heads arranged from a leading end to a trailing end. The reamer heads may increase in diameter from the leading end to the trailing end.

The leading end may be for penetration or insertion end of the K-wire into a bone. The leading end may have a tip for perforating a bone. The tip may be pointed. Alternatively, the tip may be round and feature cutting grooves therein.

The position of the reamer head or first reamer head on the K-wire may be chosen to leave a trailing end portion of the K-wire sticking out of the reamed bone.

According to a further aspect of the present invention, a kit is provided comprising a surgical nail according to the invention, a proximal aiming arm and a distal aiming arm. An advantage of the kit is the attachment of a proximal and a distal aiming arm, which prevents the nail from being displaced within the bone due to detaching a single aiming arm from one end and attaching the same at the other end of the nail.

In another exemplary embodiment, the kit further comprises a reamer according to the invention.

According to a further aspect of the invention, there is provided a method for bone fixation, particularly of a clavicle using the surgical nail according to the invention and comprising the following steps:

a. inserting the surgical nail, particularly the clavicle nail into a fractured bone at an acute angle with respect to the longitudinal axis of the bone after fragment alignment, wherein a proximal opening in a first bone fragment and a distal opening in a second bone fragment is established in the bone;
b. attaching the distal aiming arm to the distal end of the nail body;
c. attaching the proximal aiming arm to the proximal end of the nail body;
d. drilling the proximal locking holes into the bone by guiding a drill-bit by means of the proximal aiming arm;
e. advancing the proximal locking screws into the bone through the guide bores in the proximal aiming arm;
f. drilling the distal locking holes into the bone by guiding a drill-bit by means of the distal aiming arm;
g. advancing the distal locking screws into the bone through the guide bores in the distal aiming arm;

h. removing the proximal and distal aiming arm; and i. closing the two incisions in the patient's body.

One advantage of the method is that each aiming guide may be attached to one end of the nail body so that each aiming guide has to bridge only a short distance to the respective locking apertures. This configuration of a proximal and a distal aiming arm provides accurate alignment of guide holes in the aiming min with the locking apertures of the nail body, particularly for the distal guide bores relative to the distal locking apertures when the nail is bent or twisted during insertion into the bone. Another advantage of the method is that the attachment of both a proximal and a distal aiming arm prevents the nail from being displaced within the bone due to detaching a single aiming arm from one end and attaching the same at the other end of the nail.

Preferably, the method is applied for fixation of a fractured clavicle. Thereby, in a preferred first embodiment of the method the clavicle nail is inserted into a clavicle from an antero-medial to postero-lateral direction. The clavicle nail is inserted into the clavicle with the proximal end of the nail body located at the medial end portion of the clavicle and with the distal end of the nail body located at the lateral end portion of the clavicle. Preferably, before insertion of the nail, a hole may be formed in the fractured clavicle after fragment alignment from antero-medial to postero-lateral and at an acute angle to the medullary canal of the clavicle, preferably by using the surgical reamer according to the invention.

In a second embodiment the clavicle nail may be inserted from postero-lateral to antero-medial. In this case the clavicle nail is inserted into the clavicle with the proximal end of the nail body located at the lateral end portion of the clavicle and with the distal end of the nail body located at the medial end portion of the clavicle.

Preferably, before insertion of the nail, a hole is formed in the fractured clavicle after fragment alignment from postero-lateral to antero-medial and at an acute angle with respect to the medullary canal of the clavicle, preferably by using the surgical reamer according to the invention.

In another exemplary embodiment, the method further comprises the steps of pushing the surgical nail into the bone distally so that the one or more distal locking apertures protrude from the surface of the bone, verifying the alignment of the guide bores in the distal aiming arm with respect to at least one of the distal locking apertures of the surgical nail and pulling the nail body of the surgical nail proximally into the so that the proximal end of the nail body protrudes from the surface of the bone. An advantage of this embodiment of the method is the alignment of the guide bores of a distal aiming arm attached to the distal end of the surgical nail can be verified after insertion of the surgical nail into a bone and corrected if necessary.

In again a further exemplary embodiment the method further comprises the step of cutting off a portion of the proximal and distal rods extending proximally and distally beyond a proximal and distal surface of the bone, respectively, at the bone interface. Alternatively, or in addition, the method comprises removing a portion of one or each connection element that is removably coupled to the nail body.

In yet a further exemplary embodiment the method further comprises the step of placing the end cap on an external thread at the proximal end of the nail body.

According to an exemplary embodiment of the method for fixation of a fractured clavicle by inserting a clavicle nail from antero-medial to postero-lateral, the method comprises the steps of:

1) selecting a suitable clavicle nail, particularly with regard to the length and the diameter of the surgical nail as well as with regard to the distance between the proximal and distal locking apertures;
2) connecting the clavicle nail to an insertion handle;
3) inserting the clavicle nail into the fractured clavicle after fragment alignment from antero-medial to postero-lateral. Two small skin-incisions are necessary. The clavicle nail is inserted laterally so that the distal portion comprising the distal locking apertures protrudes from the lateral end portion of the clavicle;
4) placing the distal aiming arm over the distal rod of the clavicle nail;
5) positioning the distal aiming arm so that it abuts against the shoulder at the transition between the distal rod with a smaller diameter d and the nail body with a diameter D>d and tightening of the fixation screw for locking the distal aiming arm to the clavicle nail;
6) engaging the fixation screw of the distal aiming arm into the notch in the distal rod of the clavicle nail for rotational and axial alignment to the corresponding distal locking apertures of the clavicle nail;
7) inserting the protection sleeve into a guide bore in the distal aiming arm;
8) verifying the alignment of the guide bores in the distal aiming arm with a drill-bit passing through the protection sleeve and into the respective one of the distal locking apertures. For this control step the clavicle nail was pushed through the clavicle as far laterally so that the distal portion comprising the distal locking apertures protrudes from the lateral end portion of the clavicle;
9) removing the protection sleeve and the drill-bit. Then, the nail body of the clavicle nail with the distal aiming arm attached is pulled medially into the clavicle as far as the external thread at the proximal end of the nail body protrudes from the medial end portion of the clavicle using the insertion handle;
10) placing the proximal aiming arm over the proximal coupling portion of the clavicle nail;
11) locking the proximal aiming arm with the fixation screw;
12) drilling the proximal locking holes into the clavicle by guiding a drill-bit by means of the protection sleeve inserted into the respective guide bore in the proximal aiming arm;
13) placing the proximal locking screws through the protection sleeve inserted into the respective guide bore in the proximal aiming arm;
14) drilling the distal locking holes into the clavicle by guiding a drill-bit by means of the protection sleeve inserted into the respective guide bore in the distal aiming arm;
15) placing the distal locking screws through the protection sleeve inserted into the respective guide bore in the distal aiming arm;
16) removing the proximal and distal aiming arm;
17) cutting off of the distal rod at the bone interface and cutting off the proximal rod at the proximal end behind the external thread of the nail body;
18) placing the end cap onto the external thread of the nail body, protecting the proximal end of the nail body from bone ingrowth; and
19) closing the medial and lateral incision in the patient's body.

According to an exemplary embodiment, the clavicle nail may be removed from the clavicle by:

i. removing the end cap from the proximal end of the nail body of the clavicle nail;
ii. attaching the removal instrument to the external thread at the proximal end of the nail body. The locking screws have to remain in place to prevent the clavicle nail from rotation during attachment of the removal instrument;
iii. removing the locking screws; and
iv. removing the clavicle nail from the clavicle.

BRIEF DESCRIPTION OF THE DRAWINGS

Several embodiments of the invention will be described in the following by way of example and with reference to the accompanying drawings in which:

FIGS. 4-22 illustrate a perspective view of the method for bone fixation according to the invention;

FIG. 28 illustrates a lateral view of an embodiment of the reamer according to the invention;

FIG. 29 illustrates a magnified view of the front portion of the embodiment of the reamer according to FIG. 28;

FIG. 30 illustrates a magnified view of the rear portion and the reamer head of the embodiment of the reamer according to FIG. 28;

FIG. 35 illustrates a perspective view of a second embodiment of the surgical nail according to the invention;

FIG. 39 illustrates a perspective view of a fourth embodiment of the surgical nail according to the invention;

FIG. 40 illustrates a side view of the surgical nail of FIG. 39;

FIG. 45 illustrates a perspective view of an alternate embodiment of the reamer of FIG. 44;

FIG. 52 illustrates a perspective view of an end cap according to another exemplary embodiment of the present invention;

FIG. 53 illustrates another perspective view of the end cap of FIG. 52;

FIG. 54 illustrates a longitudinal cross-sectional view of the end cap of FIG. 52;

FIG. 55 illustrates a side view of the end cap of FIG. 52 and a surgical nail according to an exemplary embodiment of the present invention;

FIG. 56 illustrates a side view of the end cap of FIG. 52 and a surgical nail according to another exemplary embodiment of the present invention;

DETAILED DESCRIPTION

Figure 1:
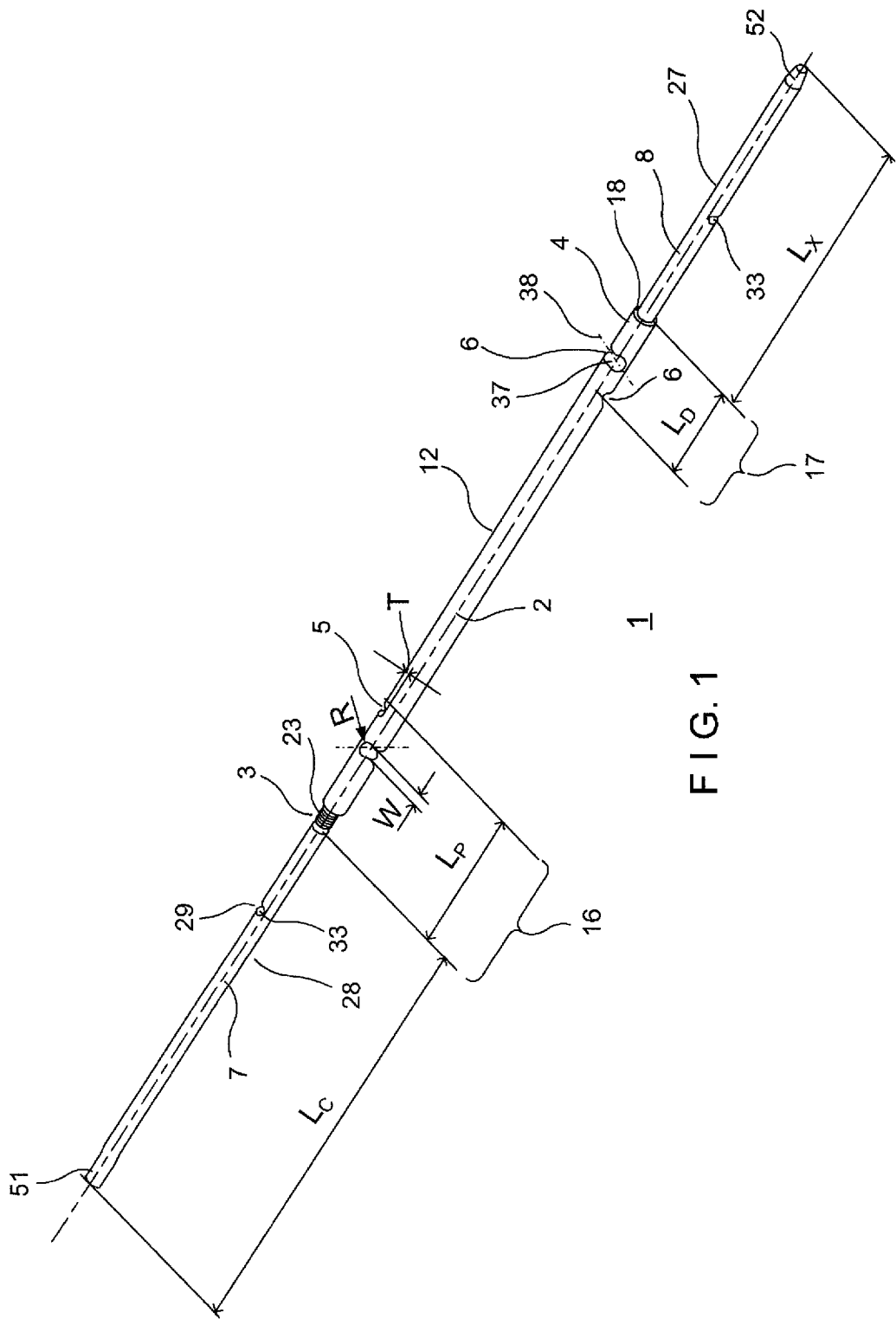
FIG. 1 illustrates a perspective view of a first embodiment of the surgical nail according to the invention.

The present invention may be further understood with reference to the following description and the appended drawings, wherein like elements are referred to with the same reference numerals. The present invention relates to the treatment of bone fractures and, in particular, relates to devices for fixing clavicle bone fractures. Exemplary embodiments of the present invention describe a nail that may be inserted along a length of a clavicle bone to fix a fracture thereof. The nail may be fixed within the bone using an aiming device to guide drilling instruments and/or bone fixation elements through the bone and into corresponding locking apertures of the nail. It should be noted that the terms "proximal" and "distal" as used herein, are intended to refer to a direction toward (proximal) and away from (distal) a user of the device. It should also be noted that the terms "medial" and "lateral" as used herein are intended to indicate a direction toward (medial) and away from (lateral) a midline of the body of a patient within which a nail is to be implanted.

Figure 27:
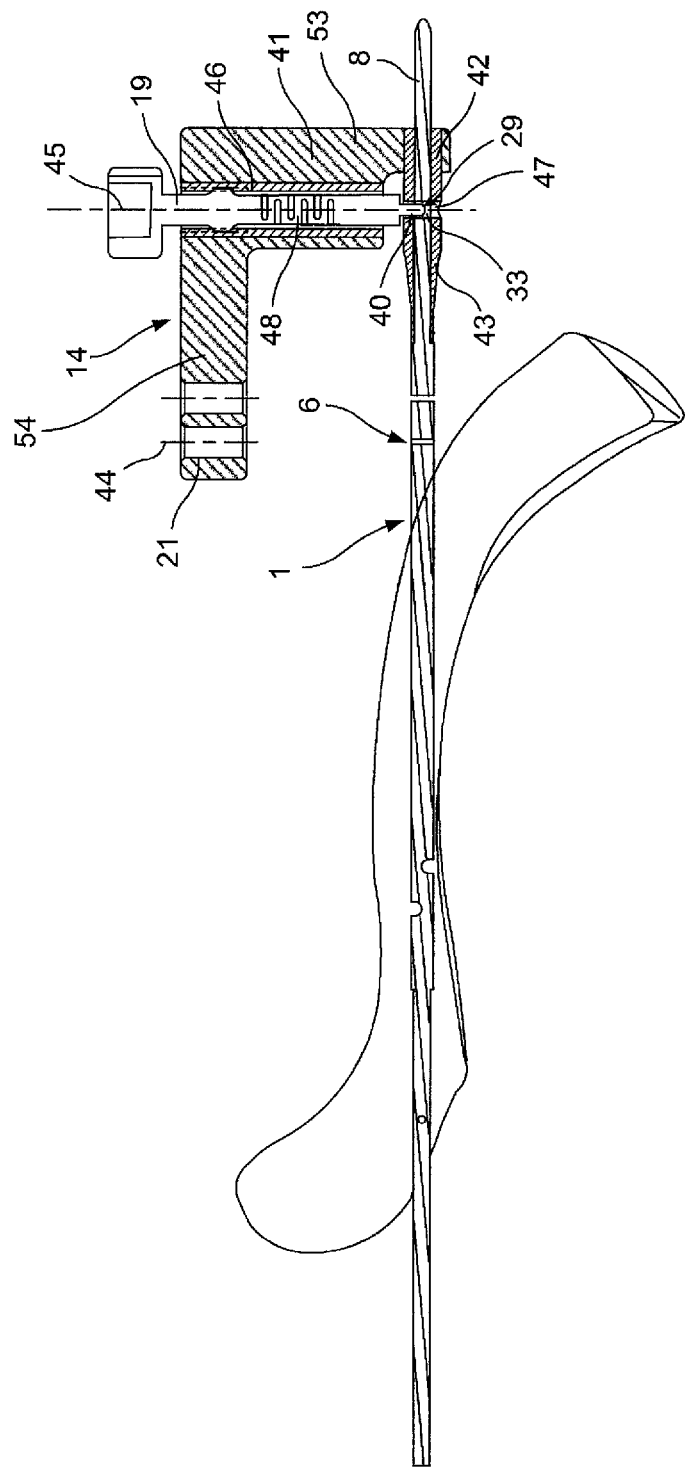
FIG. 27 illustrates a cross-section through the surgical nail and the distal aiming arm of a further embodiment of the kit according to the invention.

As shown in FIGS. 1-22, a system and method according to a first embodiment of the present invention comprises a clavicle nail 1 sized and shaped for insertion into a clavicle 9 to fix a fracture thereof. The nail 1 may be inserted into the clavicle 9 using a handle 15 and fixed therein by inserting bone fixation elements such as locking screws 24 through the clavicle 9 and into proximal and distal locking apertures 5, 6 of the nail 1. The system may further comprise proximal and distal aiming devices 13, 14, as shown in FIG. 27, which may be attached to the nail 1, for aligning a drill and/or the bone fixation elements with corresponding ones of the proximal and distal locking apertures 5, 6. In a further embodiment, the system may further comprise a reamer 30, as shown in FIGS. 28-32, for drilling a hole 32 through the clavicle 9 within which the nail 1 is to be accommodated.

Figure 2:
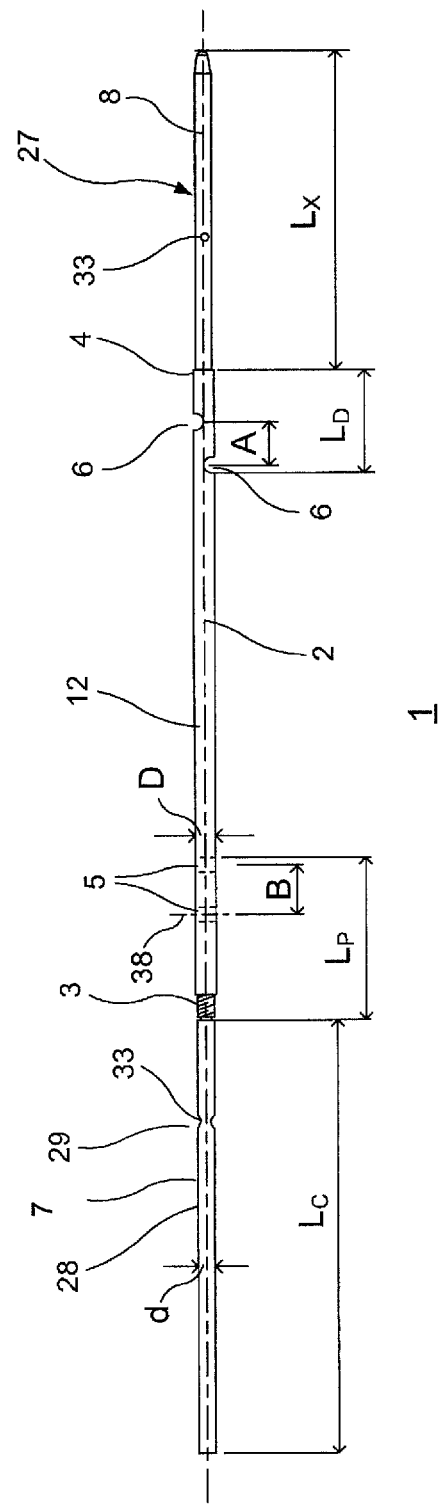
FIG. 2 illustrates a lateral view of the first embodiment of the surgical nail according to FIG. 1.
Figure 3:
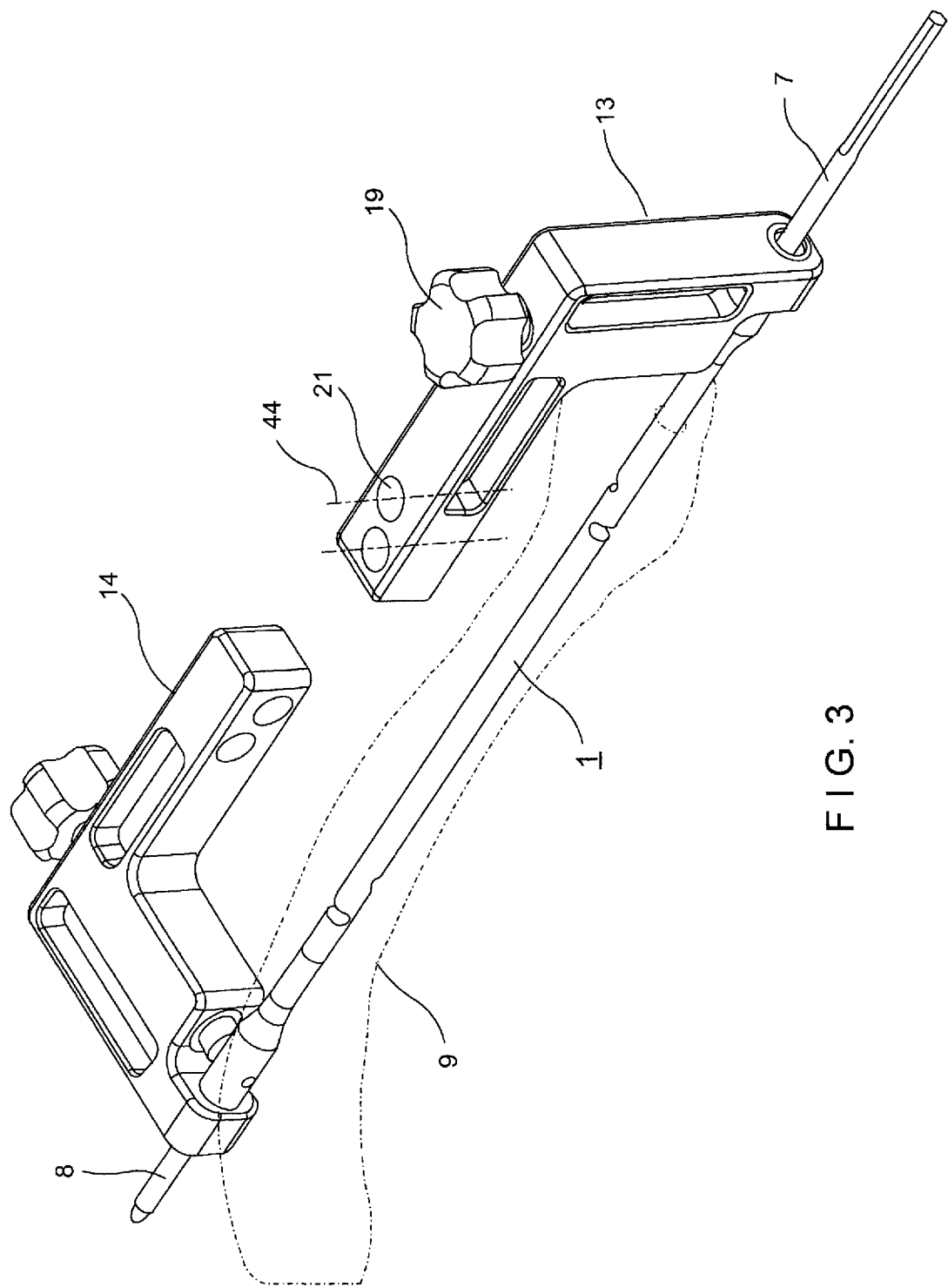
FIG. 3 illustrates a perspective view of an embodiment of the kit according to the invention.

As shown in FIGS. 1-3, the nail 1 includes a nail body 12 extending along a longitudinal axis 2 from a proximal end 3 to a distal end 4 along with a proximal connecting element 28 at the proximal end 3 and a distal connecting element 27 at the distal end 4 for coupling the proximal and distal aiming arms 13, 14, respectively, to the nail body 12. The proximal locking apertures 5 and the distal locking apertures 6 extend transversely through the nail body 12 proximate the proximal and distal ends 3, 4, respectively, for locking the nail body 12 relative to the clavicle 9. Upon fixation of the nail body 12 within the clavicle 9, the proximal and distal connecting elements 28, 27 may be cut off and/or removed from the nail body 12.

The nail body 12 may be sized and shaped for insertion into the medullary canal of the clavicle 9. The size of the medullary canal can be adapted to suit particular patient anatomies and the amount of flexibility required due to the shape of the clavicle. For example, if the diameter of a patient's clavicle is small, the nail body 12 chosen will have a smaller diameter. In another example, if the patient's clavicle is more curved than the average clavicle, then a smaller diameter nail body 12 is chosen to provide additional flexibility. In exemplary embodiments, diameters ranging from 2.5 mm up to 5.0 mm can be provided. For example, in the exemplary embodiments, the nail body 12 may have a diameter of 2.5 mm, 3.0 mm, 3.5 mm, 4.0 mm, 4.5 mm or 5.0 mm.

Other factors may also affect the flexibility of the nail body 12. For example, the nail body 12 may be manufactured from a material having a desired Young's modulus or bending stiffness, such as titanium, stainless steel, titanium-alloys. Other factors affecting the flexibility include geometry of the plane area, for example, the shape: circular, square, flat, egg-shaped, or the diameter. The skilled person could of course combine one or more of these factors to provide a nail with the desired flexibility.

Screws that may be used with the nail body 12 also vary according to the diameter of the nail body 12. For example, in an embodiment including a nail body 12 with a diameter of 2.5 mm, the screws may have a diameter up to 2.0 mm. In an embodiment having a nail body 12 with a diameter of 3.0 mm, the screws may have a diameter up to 2.4 mm. In an embodiment having a nail body 12 with a diameter of 3.5 mm or greater, the screws may have a diameter up to 2.7 mm. It will be understood by those of skill in the art, however, that other screws sizes and diameters are also possible.

As can be seen in FIG. 3, the clavicle 9 into which the nail 1 is to be inserted has a curved shape similar to an "S", which could be described as a flattened "S" or double-curved. In this regard, the nail body 12 may also be shaped for insertion into the medullary canal of the clavicle 9. The nail body 12 may be curved to correspond to a curvature of the medullary canal of the clavicle 9. The nail body 12 has an initial, undeformed shape configured to corresponds to the shape of the clavicle 9 in which the nail body 12 will reside when it has been placed in a desired position therein. Thus, deformation of the nail body 12 during insertion into the clavicle 9 (e.g., as portions of the nail body 12 pass through parts of the clavicle 9 having shapes different from the parts in which these portions of the nail body 12 will reside) will be temporary and the nail body 12 will tend to revert to the original, undeformed shape when the nail body 12 reaches the final position. A user (e.g., surgeon) may then accurately determine the location of the proximal and distal locking apertures 106, 108 using an aiming device calibrated to the initial undeformed shape of the nail body 12. Depending on the entrance and exit point of the nail, the curvature can be C-shaped. Based on anatomical data the curvature is expected to have a radius between 90 and 150 mm. The proximal end 3 of the body 12 also includes a threaded portion 23, which may additionally be used to fix the nail 1 within the clavicle 9 and/or to aid in removal of the nail body 12, if required. An end cap 25 may also be placed over the threaded portion 23 once the body 12 has been fixed within the clavicle 9, as desired.

The nail body 12 may also be formed of an elastic material which permits some flexing during insertion of the nail 1 into the bone, but which also allows the nail body 12 to revert to its original curved shape when it has been completely inserted to a desired position within the bone. Those skilled in the art will understand that the term flexible used in this context indicates a degree of flexibility sufficient to enable the nail body 12 to deform as it is inserted through the medullary canal without damaging the clavicle 9.

The proximal locking apertures 5 extend through a proximal portion 16 of the nail body 12 at a position separated from a proximal end 3 of the nail body 12 by a distance $L_P$. The distal locking apertures 6 extend through a distal portion 17 of the nail body 12 at a distance $L_D$ from the distal end 4 of the nail body 12. As would be understood by those skilled in the art, the proximal and distal locking apertures 5, 6 may be partially circular (or any other suitable shape), extending about an angle ranging from between 45° to 270°, and open to an exterior of the nail body 12. Specifically, the proximal and distal locking apertures 5, 6 may be formed as substantially U or C-shaped grooves 37 extending through a surface of the nail body 12, each of which has a central axis 38 along which a bone fixation element may be inserted. The central axes 38 may be offset from and substantially perpendicular to the longitudinal axis 2. The grooves 37 have a depth T, a width W, which is equal to twice the radius R of the partially circular locking apertures 5, 6. Thus, the depth T is greater than the radius R but smaller than a shaft diameter of the locking screw 24 so that a locking screw 24 (FIG. 15) with a shaft diameter corresponding to the width W of the groove 37 fits into the groove 37 along the central axis 38.

In the first embodiment, the nail body 12 includes two proximal locking apertures 5 and two distal locking apertures 6. The central axes 38 of the two proximal locking apertures 5 are arranged, for example, at an angle of 90° with respect to the central axes 38 of the two distal locking apertures 6. The two distal locking apertures 6 extend through opposing sides of the nail body 12 such that the central axes 38 of the two distal locking apertures 6 are on opposite sides of the longitudinal axis 2 of the nail body 12 and are parallel to one another. In addition, the two distal locking apertures 6 may be longitudinally spaced from one another by a distance, as shown in FIG. 2. Similarly, the two proximal locking apertures 5 may extend through opposite sides of the nail body 12 such that the central axes 38 of the proximal apertures 5 are located on opposite sides of the longitudinal axis 2 of the nail body 12 and are substantially parallel to one another. In addition, the two proximal locking apertures 5 may be longitudinally spaced from one another by a distance B. In one embodiment, the distance B may be equal to the distance A. In another embodiment, the distance B may be different from the distance A by which the distal locking apertures 6 are spaced from each other. The clavicle nail 1 may be inserted into the clavicle 9 so that the central axes 38 of the distal locking apertures 6 are proximate a medial end 4 of the clavicle 9 and extend in an antero-posterior direction while the central axes 38 of the proximal locking apertures 5 are located proximate a lateral end of the clavicle 9 and extend in a sagittal direction. For example, in a preferred embodiment, the clavicle nail 1 is inserted from antero-medial to postero-lateral such the proximal locking apertures 5 are located medially while the distal locking apertures 6 are located laterally. It will be understood by those of skill in the art, however, that the nail 1 may also be inserted such that the proximal locking apertures 5 are located laterally while the distal locking apertures 6 are located medially.

The proximal connecting element 28 may include a proximal rod 7 extending proximally from a proximal end 3 of the nail body 12 to a proximal end 51 substantially coaxial with the longitudinal axis 2 of the nail body 12. The proximal end 51 of the proximal rod 7 is adapted and configured to be coupled to the handle 15 for inserting the nail 1 into the clavicle 9. The proximal end 51 may be, for example, polygonally shaped to mate with a portion of the handle 15. The distal connecting element 27 includes a distal rod 8 extending distally from the distal end 4 to a distal end 52 substantially coaxial with the longitudinal axis 2 of the nail body 12. The distal end 52 of the distal rod 8 may be conically shaped to facilitate insertion of the clavicle nail 1 into the clavicle 9. Each of the proximal and distal rods 7, 8 may include a substantially cylindrical portion having a diameter d which is smaller than a diameter D of the nail body 12 so that a shoulder 18 is formed where the proximal and distal rods 7, 8 meet the nail body 12. Alternatively, one or both of the proximal and distal rods 7, 8 may have a non-circular cross-section (e.g. a polygonal cross-section) which is no larger than a cross-section of the nail body 12 so that the proximal and distal rods 7, 8 may be easily inserted into the hole 32 formed through the clavicle 9 to accommodate the nail 1.

Each of the proximal and distal rods 7, 8 includes a notch 29 for receiving a tip 40 of a fixation screw 19 which may be used to fix the proximal and distal aiming arms 13, 14 to the proximal and distal rods 7, 8 respectively. Each notch 29 may be configured as a through bore 33 extending transversely through the proximal and distal rods 7, 8, respectively. Further, the through bore 33 in the proximal rod 7 extends along a bore axis parallel to the central axes 38 of the proximal locking apertures 5 and the through bore 33 in the distal rod 8 extends along a bore axis parallel to the central axes 38 of the distal locking holes 6. The proximal rod 7 has a length $L_C$ extending from the proximal end 3 of the nail body 12 to the proximal end 51 which may, for example, be approximately four times the length $L_D$ of the distal portion 17 in which the distal locking apertures 6 are located. The distal rod 8 has a length $L_X$ extending from the distal end 4 the nail body 12 to the distal end 52, which may, for example, be approximately two times the length $L_P$ of the proximal portion 16 in which the proximal locking apertures 5 are located. In an alternative embodiment, the length $L_X$ of the distal rod 8 may be substantially equal to the length $L_C$ of the proximal rod 7.

Figure 36:
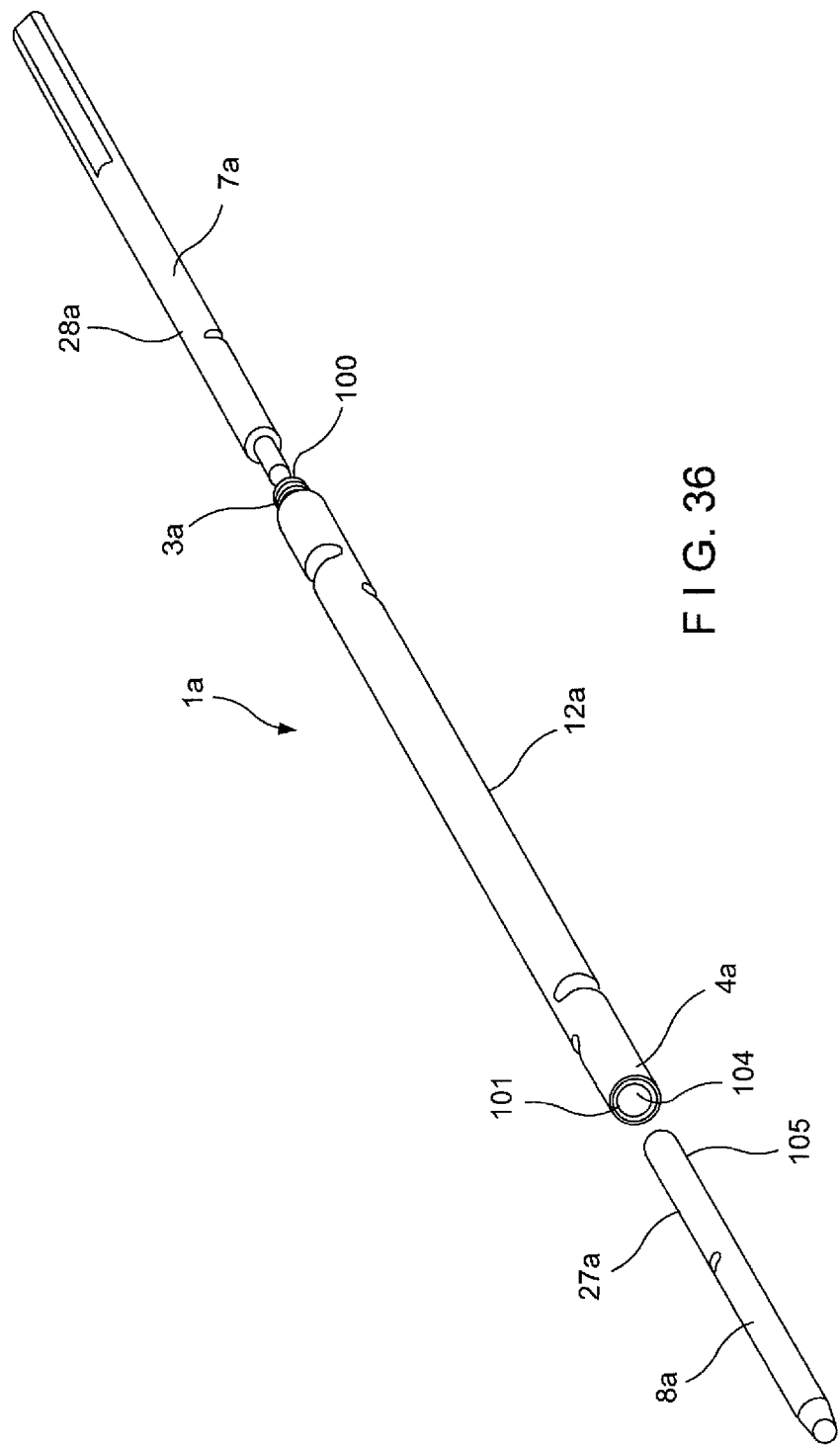
FIG. 36 illustrates another perspective view of the second embodiment of the surgical nail according to the invention.

FIGS. 35 and 36 show a nail 1a of a second embodiment of the present invention. The nail 1a may be substantially similar to the nail 1, as described, above, comprising a nail body 12a along with a distal connecting element 27a and a proximal connecting element 28a. The distal and proximal connecting elements 27a, 28a may be formed as, for example, rod-shaped distal and proximal portions 8a, 7a, respectively. It should be noted that different parts have been numbered accordingly.

In the nail 1a, the distal connecting element 27a and the proximal connecting element 28a are removably coupled to the nail body 12a. The removably coupled distal and proximal connecting elements 27a, 28a are press-fitted into openings 100, 101 formed in the distal and proximal ends 4a, 3a, respectively. The press-fit connection between the connecting elements 27a, 28a and their respective ends 4a, 3a holds these parts together by friction so that inadvertent or unexpected removal is prevented.

FIG. 35 shows the proximal end 3a having an opening 100 leading into a channel 102. The proximal connecting element 28a has a proximal element coupling portion 103 that is cylindrical in shape. The proximal element coupling portion 103 has a smaller diameter than the remainder of the proximal connecting element 28a. The opening 100 and channel 102 are sized and shaped to receive the proximal element coupling portion 103 therein and to form the press fit. In this regard, the opening 100 and channel 102 are circular in shape and have a diameter slightly less than the diameter of the proximal element coupling portion 103. It is of course possible that other shapes and configurations of the proximal element coupling portion 103 and the opening 100 and channel 102 could be used as would be understood by the person skilled in the art.

FIG. 36 shows the distal end 4a having an opening 101 into a channel 104. The distal connecting element 27a has a distal element coupling portion 105 that is cylindrical in shape. The distal element coupling portion 105 has the same diameter as the remainder of the distal connecting element 27a. The opening 101 and channel 104 are sized and shaped to receive the distal element coupling portion 105 therein and to form the press fit. In this regard, the opening 101 and channel 105 are circular in shape and have a diameter slightly less than the diameter of the distal element coupling portion 105.

It is of course possible that other shapes and configurations of either or both of the proximal and/or distal element coupling portions 103, 105 and the opening 101, 100 and channel 102, 104 could be used as would be understood by the person skilled in the art.

In an exemplary embodiment of the second embodiment, each part of the nail 1a is fabricated from the same material such as TAN. However, as will understood by the person skilled in the art the nail 1a could comprise a nail body 12a of TAN and distal and proximal connecting elements 27a, 28a fabricated from titanium or any other suitable material. Any combination of parts comprising different or the same suitable materials is of course possible as will be understood person skilled in the art.

Figure 37:
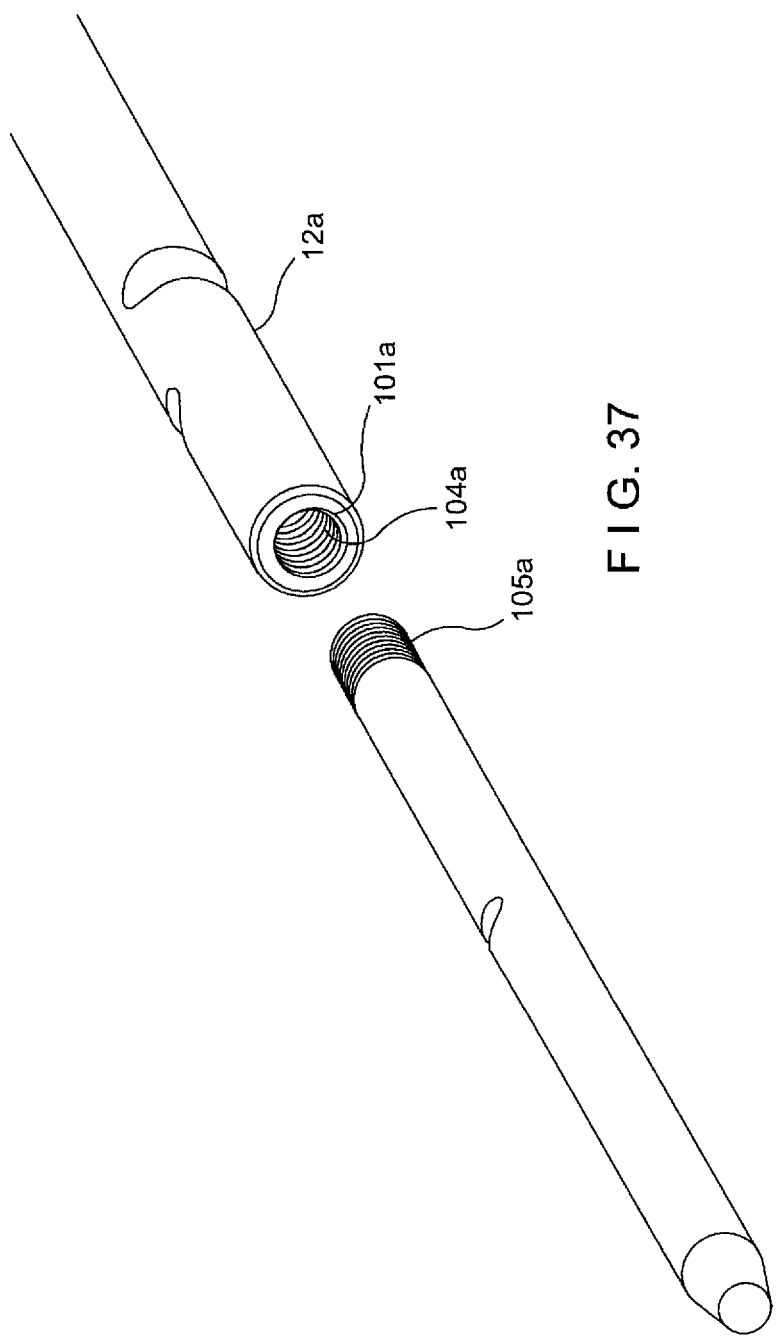
FIG. 37 illustrates a perspective view of an alternative end portion of the second embodiment of the surgical nail according to the invention.

The nail 1a has been described as having press-fitted distal and proximal connecting elements. However, other variants of removable coupling arrangement are of course possible. An example of such a variant is shown in FIG. 37 where a coupling portion 105a is externally threaded and the opening and channel 101a, 104a are internally threaded. In another variant (not shown), the removable coupling between the connection elements and the nail body use a bayonet-type connection.

In other variants (not shown) distal connecting and proximal connecting elements are welded, for example laser welded, or glued to a nail body. In these variants, the elements are coupled to the nail body with a predefined breaking force.

As will be understood by the skilled person a nail can be fabricated using any combination of the different variants of removable coupling. For example, a nail could be fabricated where the distal connection element is press-fitted into the nail body and the proximal connection element is welded to the nail body.

Figure 38:
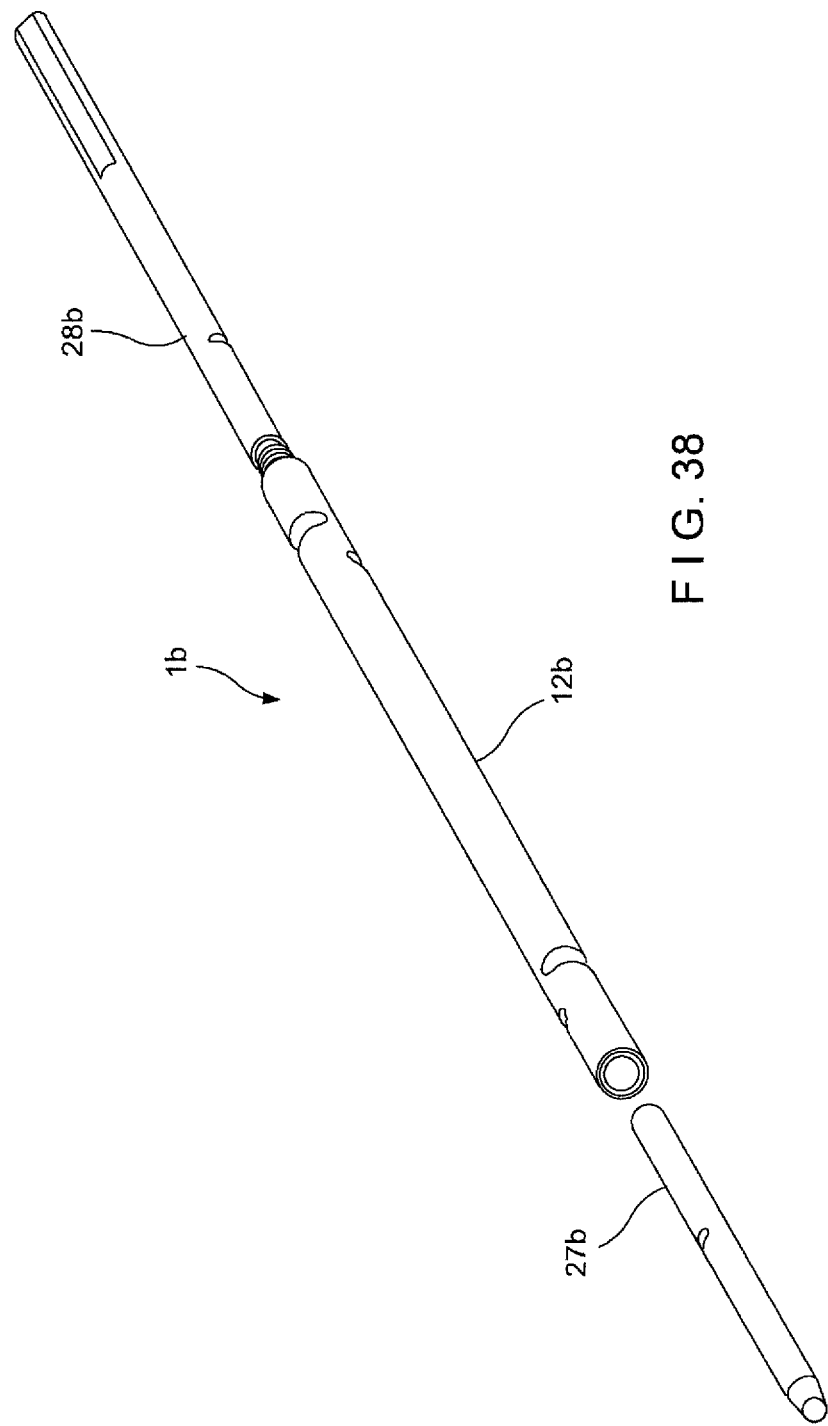
FIG. 38 illustrates a perspective view of a third embodiment according to the invention.

In a third embodiment shown in FIG. 38, a nail 1b may be substantially similar to the nails 1, 1a, as described above, but has a proximal connecting element 28b that is substantially similar to the proximal connecting element 28 as described for the first embodiment of the nail 1 and the distal connecting element 27b that is substantially similar to the distal connecting element 27a as described for the second embodiment of the nail 1a, or one of the described variants. That is, the proximal connecting element 28b is integrated with the nail body 12b and the distal connecting element 27b is removably coupled to the nail body 12b according to one of the described variants, for example, the distal connecting element 27b is press-fitted into the nail body and can be removed using an instrument (not shown).

As will be described in more detail below, in this embodiment the proximal connecting element 28b is cut off after implantation and an endcap 25 is provided to cover any sharp edges resulting from the cutting to provide soft tissue protection. After the endcap 25 is positioned, the distal end is pressed in and the distal connecting element 27b can be removed using an instrument (not shown).

According to a fourth exemplary embodiment, as shown in FIGS. 39-40, a nail 1c may be substantially similar to the nail 1 described above. Specifically, the nail 1c comprises a nail body 12c along with a proximal connecting element 28c and a distal connecting element 27c. The proximal and distal connecting elements 28c, 27c may be formed as, for example, rod-shaped proximal and distal portions 7c, 8c, respectively. The proximal and/or distal rods 7c, 8c may be keyed to a portion of the proximal and distal aiming arms 13, 14 to prevent the aiming arms 13, 14 from rotating relative to the nail 1c. For example, the proximal and distal rods 7c, 8c may include planar surfaces 107c, 108c, respectively, extending along portions thereof and corresponding to a portion of surfaces of the aiming arms 13, 14.

The proximal and/or distal connecting elements 28c, 27c may also include grooves 109 extending about distal and proximal ends, respectively, thereof to facilitate the cutting of the proximal and distal connecting elements 28c, 27c after implantation. The grooves 109 may extend about the rods 7c, 8c proximate the proximal and distal ends 3c, 4c of the nail body 12c.

Figure 41:
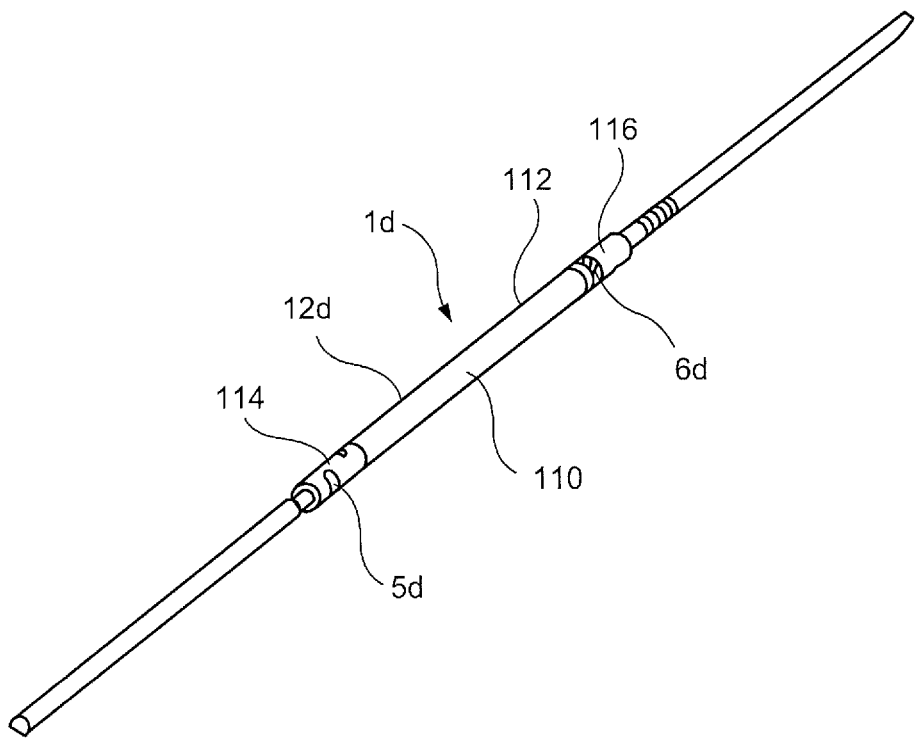
FIG. 41 illustrates a perspective view of a fifth embodiment of the surgical nail according to the invention.
Figure 42:
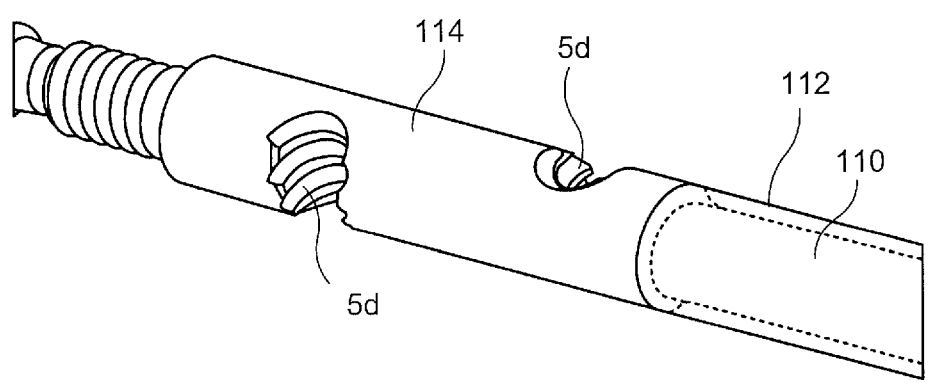
FIG. 42 illustrates an enlarged perspective view of a portion of the surgical nail of FIG. 41.

As shown in FIGS. 41-42, a nail 1d according to a further exemplary embodiment of the present invention may be substantially similar to any of the nails 1, 1a, 1b, 1c, described above. However, a nail body 12d but further includes a region of reduced diameter 110 that is overmolded with a suitable elastomer or polymer 112. The region of reduced diameter 110 may extend along the nail body 12d between proximal and distal apertures 5d, 6d such that the proximal and distal apertures 5d, 6d extend through non-reduced diameter regions 114, 116 of the nail body 12d. The non-reduced regions 114, 116 may therefore extend along proximal and distal portions of the nail body 12d. The region 110 is smaller in diameter than the regions 114, 16 to provide increased flexibility. For example, where the region 114, 116 have a diameter 2.5 mm, the reduced regions 110 may have a diameter in the range of 2.0 mm to 2.4 mm. Where the regions 114, 116 have a diameter of 3.0 mm, the reduced diameter region 110 may have a diameter in the range of 2.0 mm to 2.9 mm. Where the regions 114, 116 have a diameter of 3.5 mm, the reduced diameter region 110 may have a diameter in the range of 2.0 mm to 3.4 mm.

To produce a nail 1d having the nail body 12d, the reduced diameter region 110 is formed and the elastomer or polymer 112 is overmolded to surround the reduced diameter region 110. The elastomer or polymer 112 is a visco-elastic and a biocompatible polymer or elastomer. Examples of suitable polymers include: poly-ethylene and polyether ether ketone. Examples of suitable elastomers include: polycarbonate-urethane (PCU) and silicone. Other suitable polymers or elastomers may also be used as long as they have a Young's (E) modulus less than that of a remaining portion of the nail 1d. The overmolded elastomer or polymer 112 in addition to supporting the flexibility of the nail 1d, also prevents bony in or on-growth onto the nail body 12d which would prevent subsequent post-operative removal of the nail 1d.

Figure 50:
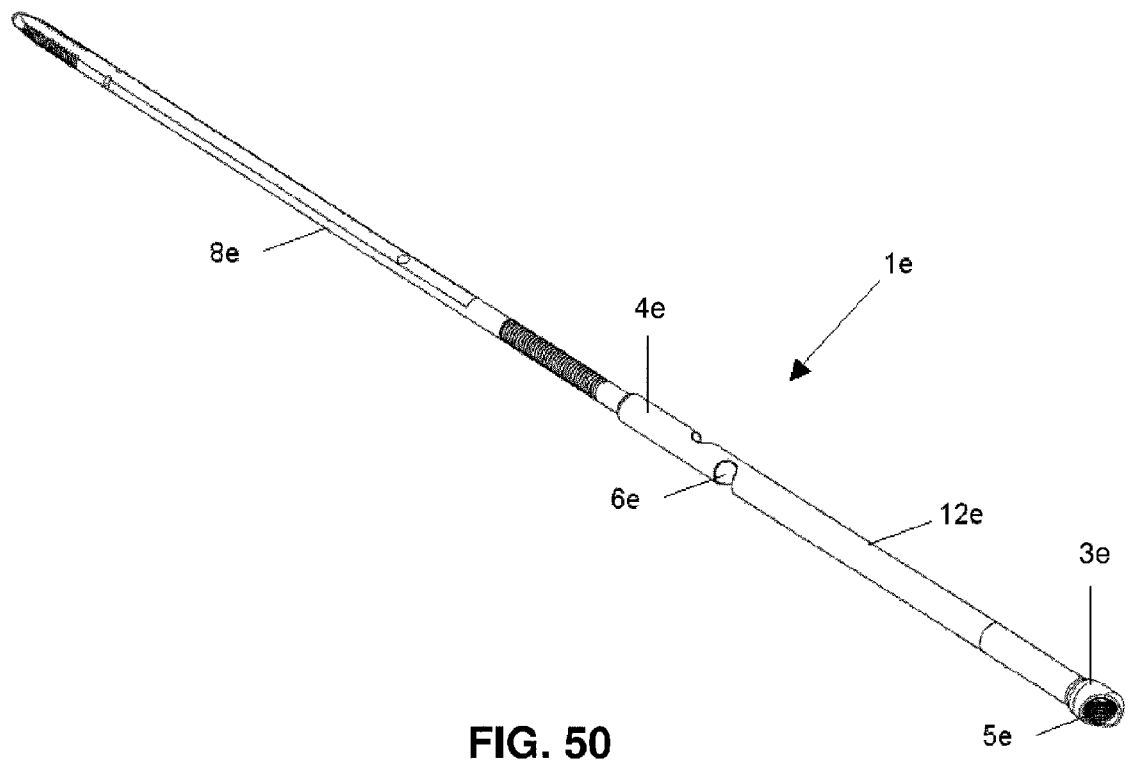
FIG. 50 illustrates a perspective view of a sixth embodiment of a surgical nail according to the invention.
Figure 51:
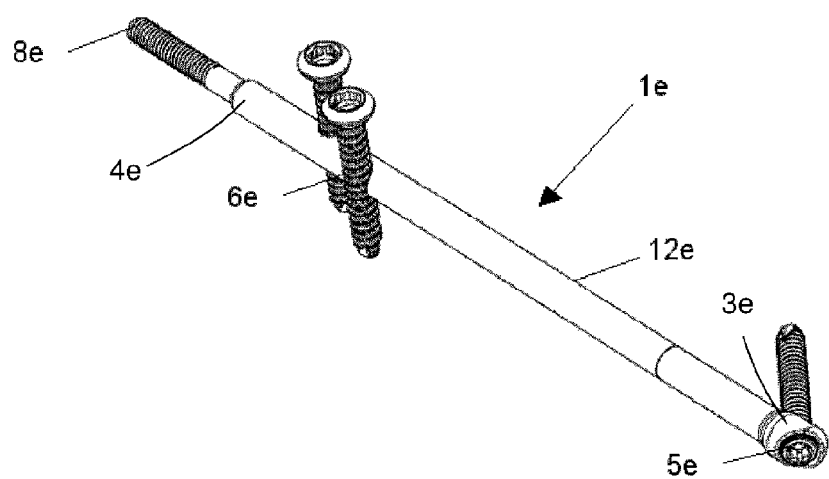
FIG. 51 illustrates a perspective view of a sixth embodiment of the surgical nail of FIG. 50 showing fixation elements in situ.

FIGS. 50 and 51 show a nail 1e of a sixth embodiment of the present invention. The nail 1e may be substantially similar to the nail 1, as described above, comprising a nail body 12e along with a distal connecting element 8e extending from a distal end 4e thereof. The distal connecting element 8e may be formed as, for example, rod-shaped distal end portions. It should be noted that different parts have been numbered accordingly.

In the sixth embodiment, the proximal end features a proximal end locking aperture 5e and has no proximal connecting element. The proximal locking aperture 5e may extend from a proximal end 3e of the nail body 12e through a wall of the nail body 12e such that the an axis of the proximal locking aperture 5e is arranged at an angle relative to the longitudinal axis of the nail 1e. Thus, a bone fixation element may be inserted through the proximal end 3e to fix the nail body 12e to the bone and a proximal aiming guide is not required to guide the bone fixation element through the proximal locking aperture 5e. The angle, relative to the longitudinal axis of the nail body 12e may be in a range of 10° to 170°. For example, the angle may be approximately 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165° or 170°. Similarly to the other embodiments, as described above, there is a relationship between the proximal locking aperture 5e and the distal locking apertures 6e. For example, with respect to a plane extending from the longitudinal axis, the axis defined by the proximal locking aperture 5e may be offset relative to an axis defined by distal locking apertures 6e. For example, the axis of the proximal locking aperture 5e may be perpendicular to the distal locking apertures 6e. Alternatively, the locking apertures may extend in the same plane. Similarly to the other embodiments described above, the distal connecting element 8e is removably coupled to the nail body 12e. The amount of distal connecting element 8e removed may be any length selected by a user. For example, the amount removed may correspond to an amount of the nail 1e a user determines is required to support healing of the clavicle in which the nail 1e is inserted.

A seventh embodiment of the nail 1f is shown in FIG. 56, the nail 1f may be substantially similar to the nail 1e, described previously. The difference is that the nail 1f has no distal locking aperture or apertures. That is, with the exception of a thread for receiving an end cap, the distal end region of the nail 1f defines a smooth surface.

FIGS. 52 to 56 show another embodiment of an end cap 80, which may be used similarly to an end cap 25 described above. The end cap 80 has a body defined by a leading end 81, a trailing end 82, an external surface 83, and an internal surface 87 defining a channel A extending through the body 80. In the trailing end 82, a drive receiving feature 86 is defined. The drive receiver 86 may be shaped and dimensioned to receive any driving device as would be understood by those skilled in the art. As shown by FIG. 54, the drive receiver 86 may be shaped, for example, to non-rotatably receive a hex-shaped drive tool therein. The end cap 80 is placed over a distal end of a nail 1, 1a, 1b, 1c, 1d, 1e, 1f by positioning the distal end in the channel A and is secured to the nail and bone for covering and locking the distal end of the nail 1, 1a, 1b, 1c, 1d, 1e, 1f to the bone.

As shown by FIG. 52, the external surface 83 has a bone engagement feature, such as an external thread 90. In a preferred embodiment, the external thread is a self-tapping thread. In the leading end region, at least one recess 84 is formed in the thread 90. The recess 84 breaks up the thread 90 in the leading end region to form a flute with a self-tapping tip 85 to provide a drill-like feature. Although the embodiment shown in FIG. 52, includes three recesses 84 in the leading end region. As those skilled in the art would understand, any number of recesses may be formed in the leading end region without departing from the scope of the invention. The recesses 84 are spaced equidistant from one another relative to a central axis passing through the body to ensure equal penetration of the end cap 80 into a bone. The end cap 80 may also include a reduced diameter portion 88 proximate the trailing end 82, which includes an engagement feature such as an external thread extending therealong. The engagement feature of the reduced diameter portion 88 may, for example, engage an internal threading of an end cap 25, as will be described in further detail below.

Figure 57:
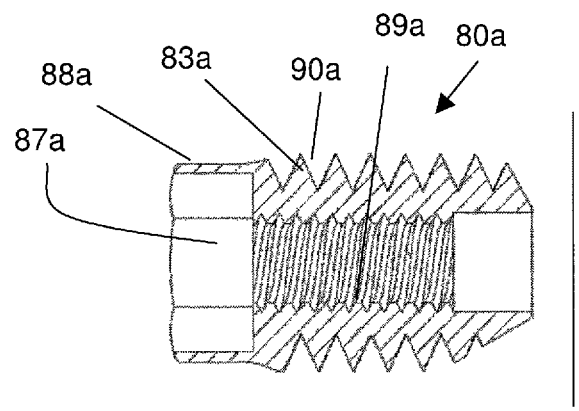
FIG. 57 illustrates a cross-sectional view of an end cap according to another embodiment of the present invention.
Figure 58:
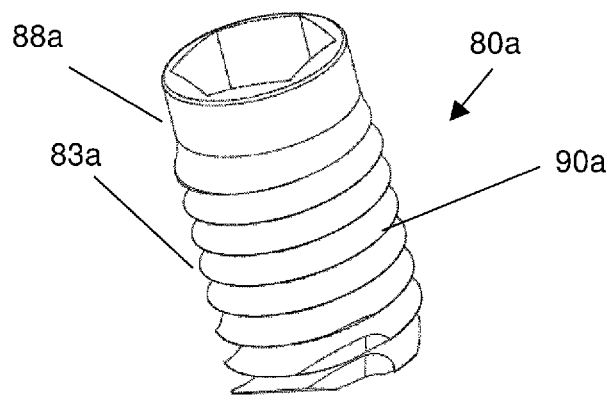
FIG. 58 illustrates a perspective view of the end cap of FIG. 57.

FIGS. 57 and 58 show another embodiment of an end cap 80a. The end cap 80a has similar features to the end cap 80. FIGS. 57 and 58 are numbered to show the features that are different between the end caps 80 and 80a. With the exception of the reduced diameter portion 88a and the engagement features, as described in more detail below. The reduced diameter portion 88a defines a featureless or smooth external surface. In use, the reduced diameter portion 88a remains uncovered after insertion into a patient.

To engage the end caps 80, 80a to the nail and the bone their respective internal and external surfaces 83, 83a, 87, 87a define engagement features. The engagement feature on the respective internal surface may be a nail engagement feature, such as an internal thread 89, 89a, and the engagement on the respective external surface may be a bone engagement feature, such as an external thread 90, 90a. As the skilled person would understand, the end caps 80, 80a may have any relationship between the respective internal and external threads 89, 89a, 90, to enable coupling of an end cap 80, 80a to a nail to lock the nail to a bone and to minimize fracturing of the bone upon insertion of the end cap. For example, for the end cap 80, the internal thread 89 has the same pitch as the thread on a distal end of a nail 1, 1a, 1b, 1c, 1d, 1e, 1f. As shown in FIG. 54, the internal thread 89 and external thread 90 in this embodiment have the same pitch. In another example, for the end cap 80a the internal thread 89a has the same pitch as the thread on a distal end of a nail 1, 1a, 1b, 1c, 1d, 1e, 1f. As shown by FIG. 58, the relationship between the internal and external threads 89a, 90a is that the external pitch is double the internal pitch. In addition, the internal thread 89a has a double lead thread and the external thread 90a has a single lead, where the lead is the same.

In use, the end cap 80, 80a is applied to a nail 1, 1a, 1b, 1c, 1d, 1e, 1f to lock an end, for example a distal end, of the nail after it has been applied to a bone (e.g., a clavicle). In a first step, the channel A is positioned over a distal connecting portion and the end cap 80, 80a is pushed along that portion until the thread on the nail 1, 1a, 1b, 1c, 1d, 1e, 1f or the outer surface of the bone is reached. A driving device is engaged with the drive receiver 86 and operated to tap the external thread 90, 90a into the bone and engage the internal thread 89, 89a with a thread on the nail. Upon completion of the driving operation, the end cap 80, 80a is secured to the nail by the internal thread 89, 89a and locked to the bone by the external thread 90, 90a. FIGS. 55 and 56 show the end cap 80 after having been coupled to a nail. Optionally, for the end cap 80, the end cap 25 may be placed over the reduced diameter portion 88 to engage the engagement feature.

As shown in FIG. 3, a kit according to a first embodiment of the present invention comprises the clavicle nail 1 along with the proximal aiming arm 13 and the distal aiming arm 14, which may be connected to the proximal and distal connecting elements 28, 27 of the clavicle nail 1 after the nail 1 has been inserted through the clavicle 9 as will be described below. The proximal aiming arm 13 and the distal aiming arm 14 may be substantially identically configured so that the detailed description of the distal aiming arm 14 also applies to the proximal aiming arm 13.

As illustrated in FIG. 27, the distal aiming arm 14 comprises a substantially L-shaped body 41 including first and second extensions 53, 54 angled relative to one another, in a preferably perpendicular configuration. The distal aiming arm 14 includes a sleeve 42 at an end of the first extension 53 of the L-shaped body 41 such that the sleeve 42 extends substantially parallel to the second extension 54. The sleeve 42 includes a central bore 43 for slidably receiving the distal rod 8 of the clavicle nail 1 and a transverse bore 47 extending therethrough to accommodate a tip 40 of a fixation screw 19, which passes therethrough to fix the distal aiming arm 14 relative to the distal rod 8 of the clavicle nail 1. The first extension 53 may also include a lumen 46 extending along a length thereof and in communication with the transverse bore 47, permitting the fixation screw 19 to be inserted into the lumen 46 so that the tip 40 may extend through the transverse bore 47 to fix the distal arm 14 relative to the distal rod 8. The second extension 50 of the L-shaped body 41 includes guide bores 21 each of which extends along a bore axis 44. The guide bores 21 extend through the second extension 54 transversely relative to a length thereof. The guide bores 21 may extend through the second extension 54 such that each of the bore axes 44 correspond to the central axes 38 of the distal locking apertures 6 in the clavicle nail 1.

The fixation screw 19 may be threadably received in the lumen 46 so that a screw axis 45 of the fixation screw 19 is substantially parallel to the bore axes 44 of the guide bores 21. The fixation screw 19 comprises a knurled end portion, a tip 40 that may be inserted through the transverse bore 47 and into the notch 29 of the distal rod 8, which, as described above, may be a through bore 33 extending transversely through the distal rod 8. A shaft of the fixation screw 19 may be made flexible along a length thereof via, for example, a plurality of grooves 48 extending around a portion of a circumference of the shaft. Thus, the fixation screw 19 may be tightened against the distal rod 8 even when the tip 40 of the fixation screw 19 is not aligned with the notch 29, permitting the distal aiming arm 14 to be axially and rotatably adjusted until the tip 40 of the fixation screw 19 snaps into the notch 29 in the distal rod 8 of the clavicle nail 1.

Figure 49:
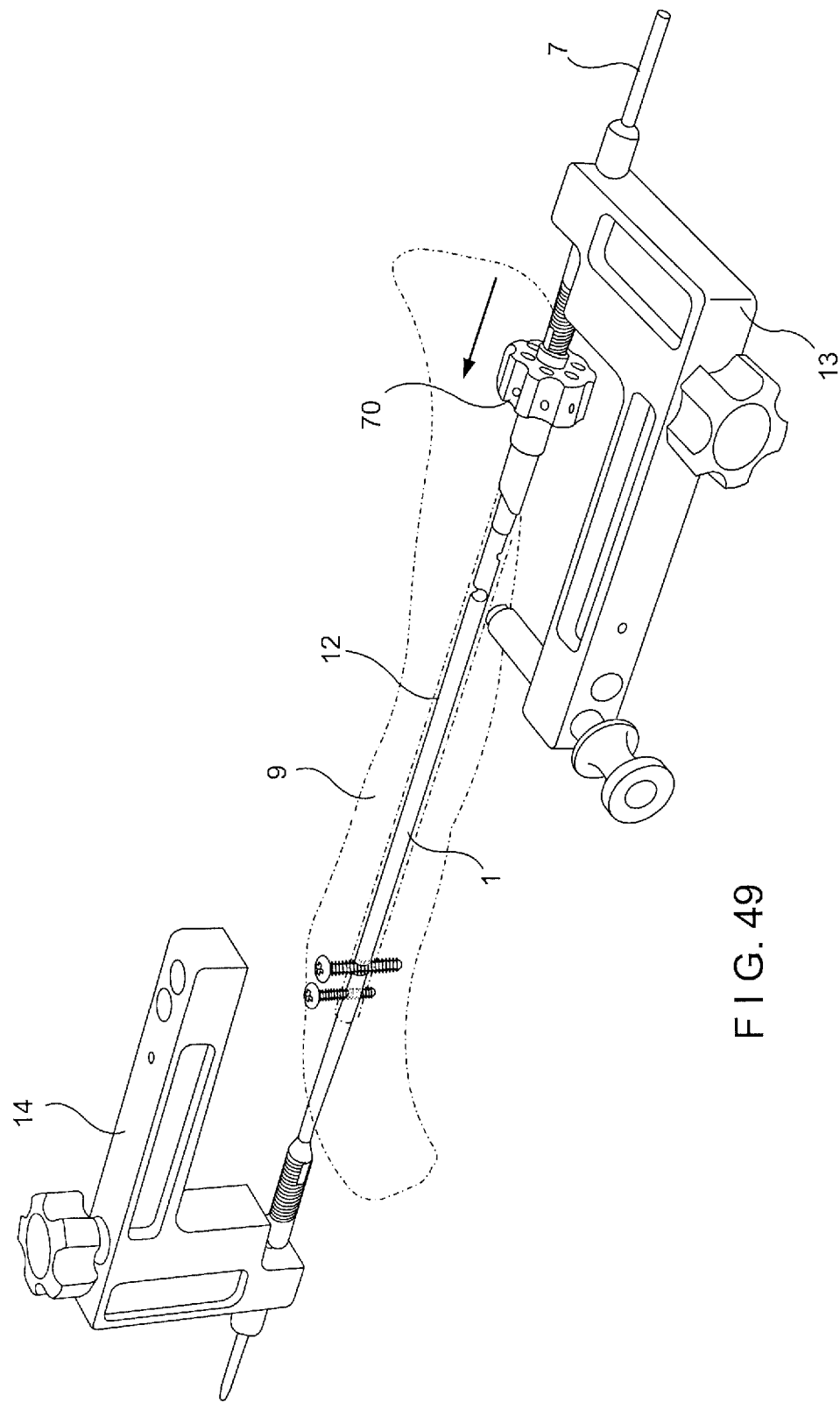
FIG. 49 illustrates a perspective view of a system according to another exemplary embodiment of the invention.

In a further embodiment, as shown in FIG. 49, the proximal aiming arm 13 may be couplable to a compression nut 70 for providing compression to the fracture of the clavicle 9. The compression nut 70 may be rotatably coupled to the a portion of the aiming arm 13, which receives the proximal rod 7 such that rotation of the compression nut 70 relative to the aiming arm 13, moves the nut 70 longitudinally relative to the aiming arm 13.

As would be understood by the skilled person, the kit 3 could alternatively comprise the nail 1a, 1b, 1c, 1d or one of the variants, or the kit could comprise a selection of nails of a single embodiment or a combination of embodiments.

As shown in FIGS. 28-34, the surgical reamer 30 which may be used to form a hole 32 in the clavicle 9 to accommodate the nail 1, comprises a K-wire 41 extending along a longitudinal axis from a distal end 50 to a proximal end portion 35. The proximal end portion 35 includes a reamer head 34 integrally formed with the K-wire 41 distally of a proximal end 49 thereof. However, those skilled in the art will understand that the reamer head 34 may be formed as a separate member coupled to the K-wire 41. The proximal end 49 and the distal end 50 may have a generally polygonal cross section such that the proximal and/or distal ends 49, 50 may engage a drilling or other machine to provide torque to the reamer 30. In a preferred embodiment, the proximal and distal ends 49, 50 have three flat sides extending along a length thereof allowing for better torque transmission of the drilling machine to the reamer 30. The reamer head 34 has a diameter substantially corresponding to the diameter D of the nail body 12 of the clavicle nail 1. Furthermore, the reamer head 34 has cutting-flutes configured, for example, in a left-hand manner when viewed in a direction along the longitudinal axis of the reamer 30 from the proximal end 49. Thus, it is possible for the distal end 50 of the reamer 30 to be coupled to a drilling machine such that the reamer 30 may be pulled through the clavicle 9. In addition, it is also possible to couple the proximal end 49 to a drilling machine such that the reamer 30 may be pushed through the clavicle 9.

Figure 31:
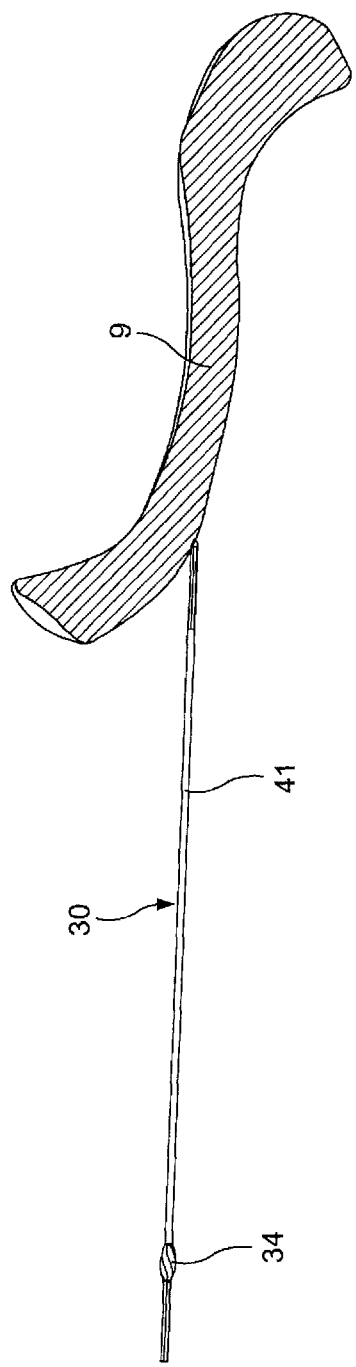
FIGS. 31 to 34 illustrate the application of the embodiment of the reamer according to FIG. 28.
Figure 32:
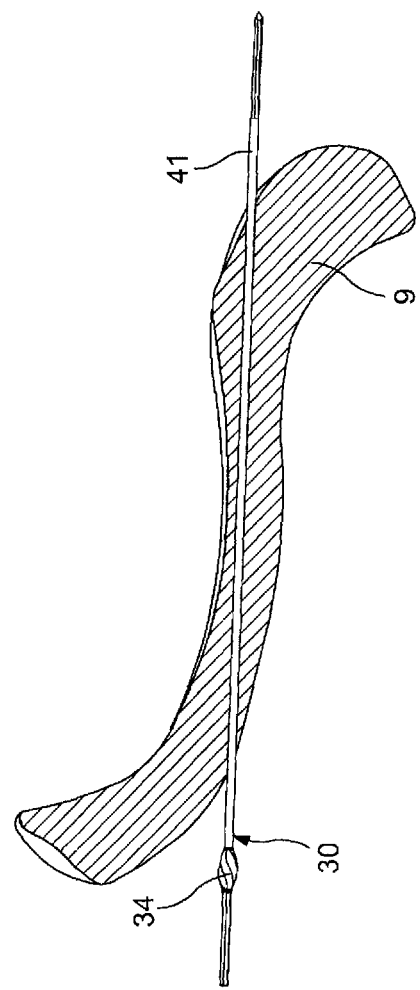
Figure 33:
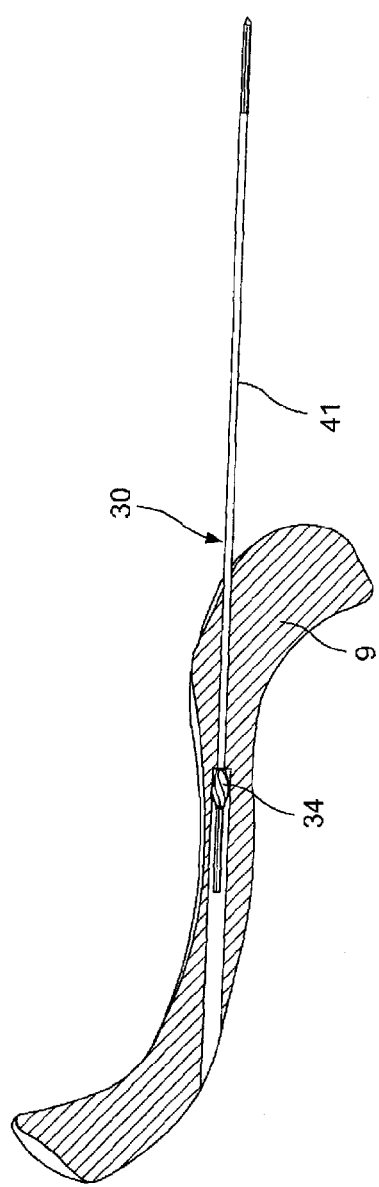
Figure 34:
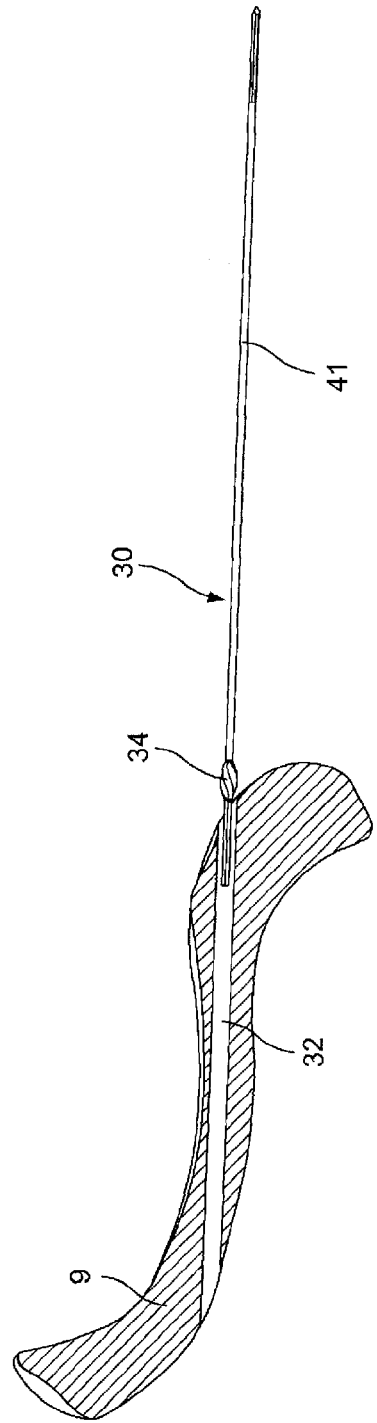

As illustrated in FIGS. 31 and 32, the portion of the K-wire 41 distal of the reamer head 34 is being pressed or drilled through the clavicle 9 as would be understood by those of skill in the art. For example, a power tool or drilling machine may be coupled to the proximal end 49 to move the k-wire 41 through the clavicle 9. A length of the K-wire 41 defines a trajectory of the reamer 30. Once the reamer head 34 contacts a surface of the clavicle 9, the power tool or drilling machine is removed from the proximal end 49 of the reamer 30 and coupled to the distal end 50 of the reamer 30. Subsequently, as illustrated in FIGS. 33 and 34, the reamer head 34 of the reamer 30 is pulled and drilled through the clavicle 9 to drill the hole 32 in the clavicle 9 for insertion of the clavicle nail 1. To have a right hand rotation of the reamer 30 when the drilling machine is attached to the foremost portion 50 of the reamer 30, the cutting-flutes of the reamer head 34 are designed in a left-hand manner. It will be understood by those of skill in the art, however, that the cutting flutes may be in any of a variety of configurations so long as the reamer head 34 facilitates drilling of the hole 32 through the clavicle 9.

Figure 43:
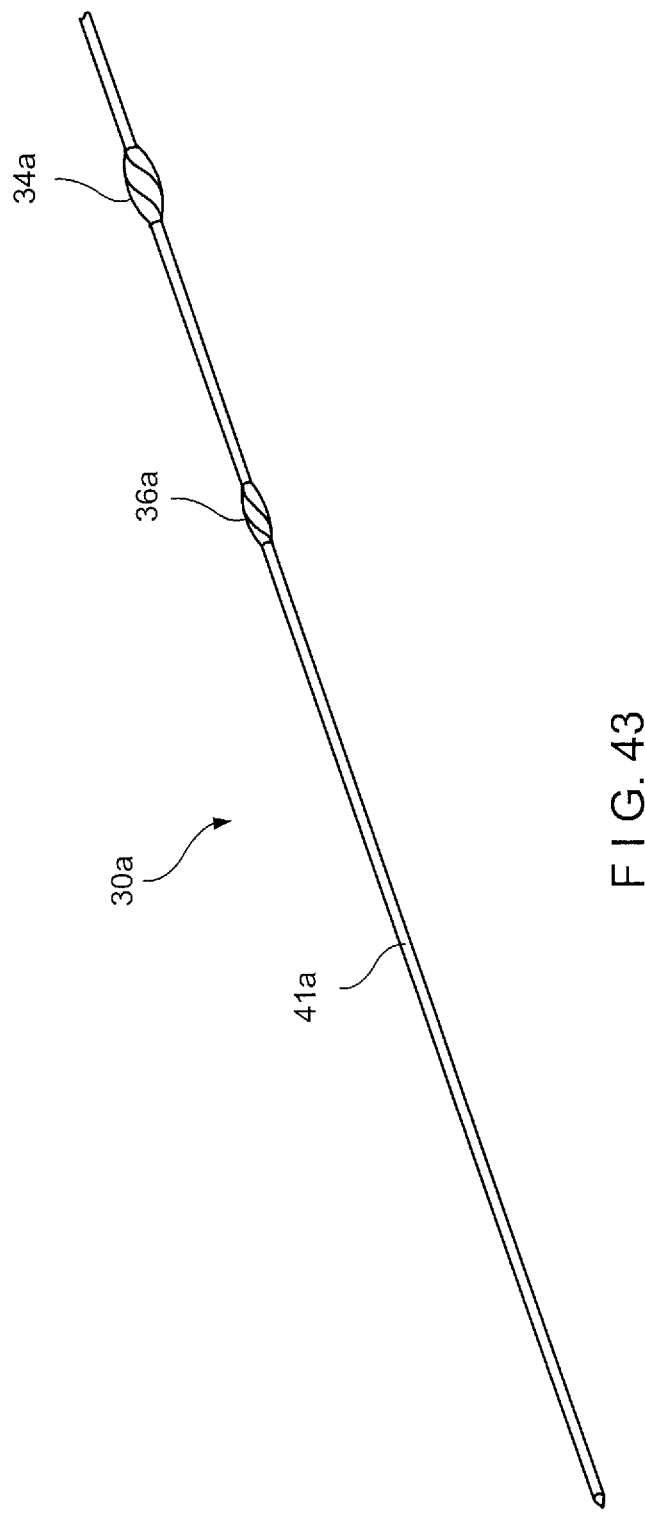
FIG. 43 illustrates a perspective view of a second embodiment of the reamer according to the invention.

In another embodiment, as shown in FIG. 43, a reamer 30a similarly includes a K-wire 41a and a first reamer head 34a. However, in this embodiment, the reamer 30a further includes a second reamer head 36a distal of the first reamer head 34a by a predetermined distance and having a smaller diameter than the first reamer head 34a. The distance between the first and second reamer heads 34a, 36a provides room for reamed bone material to reside therebetween. In addition, the two reamer heads 34a, 36a decrease the force required to pull the reamer 30a through the bone.

Figure 44:
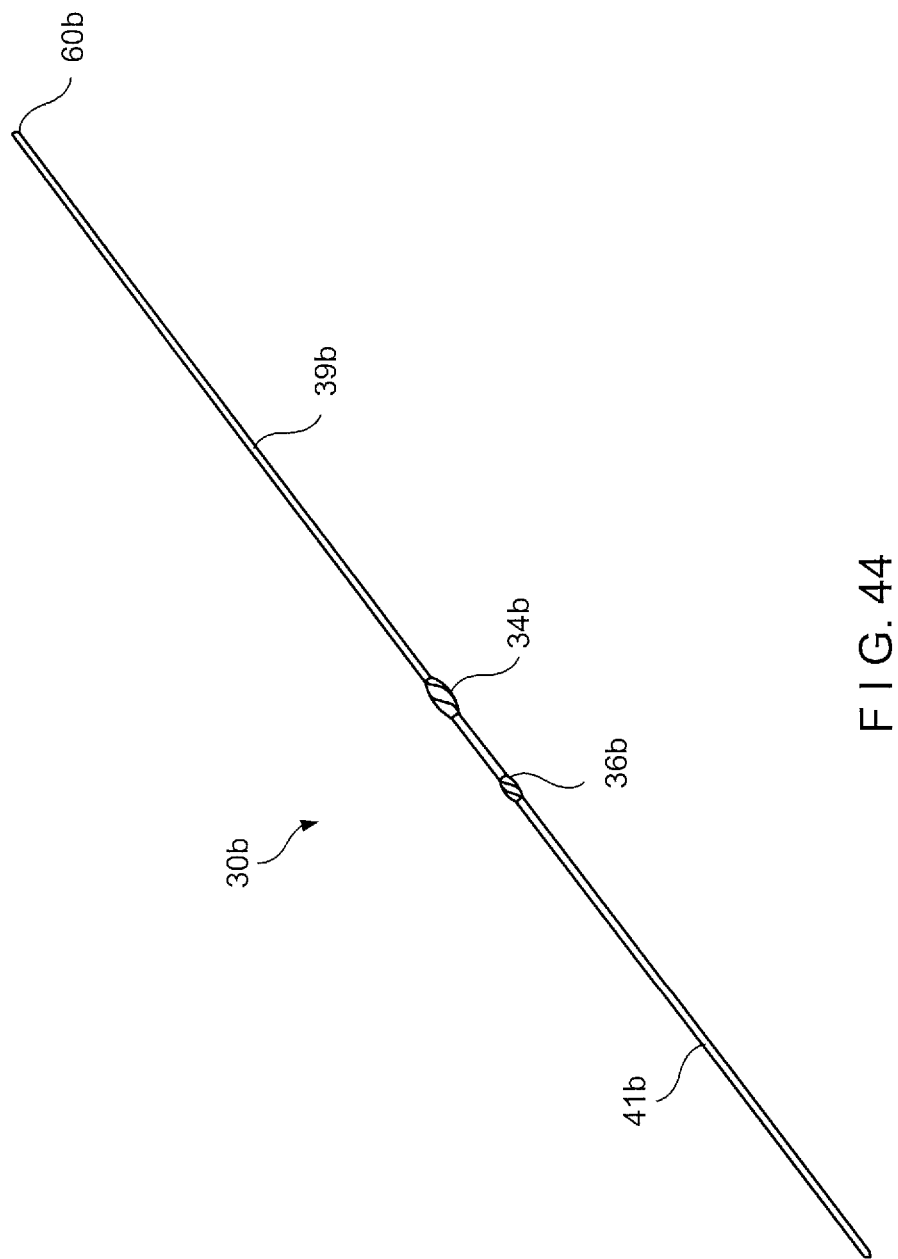
FIG. 44 illustrates a perspective view of a third embodiment of the reamer according to the invention.

In a further embodiment, as shown in FIG. 44, a reamer 34b is substantially similar to the reamer 30a comprising a K-wire 41b along with first and second reamer heads 34b, 36b, respectively. This reamer 34b further comprises a proximal portion 39b extending proximally from the first reamer head 34b for maintaining reduction of the clavicle 9. The proximal portion 39b may be a wire, as shown in FIG. 44, or alternatively, a cable as shown in FIG. 45. Specifically, after the K-wire 41b and the first and second reamer heads 34b, 36b are drawn distally through the clavicle 9, the proximal portion 39b remains in the bone 9 to maintain the reduction. A proximal end 60b of the proximal portion 39b is configured for attachment to the distal end 52 of the nail 1, as shown in FIG. 45. For example, the proximal end 60b may include a female threaded component, such as a nut. The female threaded component may be coupled to a corresponding male thread provided on the distal end 52 so that the proximal portion 39b may be pulled through the clavicle 9 to implant the nail 1 therein. As one of ordinary skill in the art would understand, other means for coupling the cable and the implant are also possible.

Alternatively, the proximal portion 60b may serve as a guide wire over which the nail 1 is inserted. The proximal portion 60b may be inserted through a channel of the nail 1 such that the nail 1 may be slid over the proximal portion 60b and into the clavicle 9 therealong. Once the nail 1 has been properly implanted, the proximal portion 60b may be removed as would be understood by those skilled in the art.

Figures 19, 20, 21, 22:
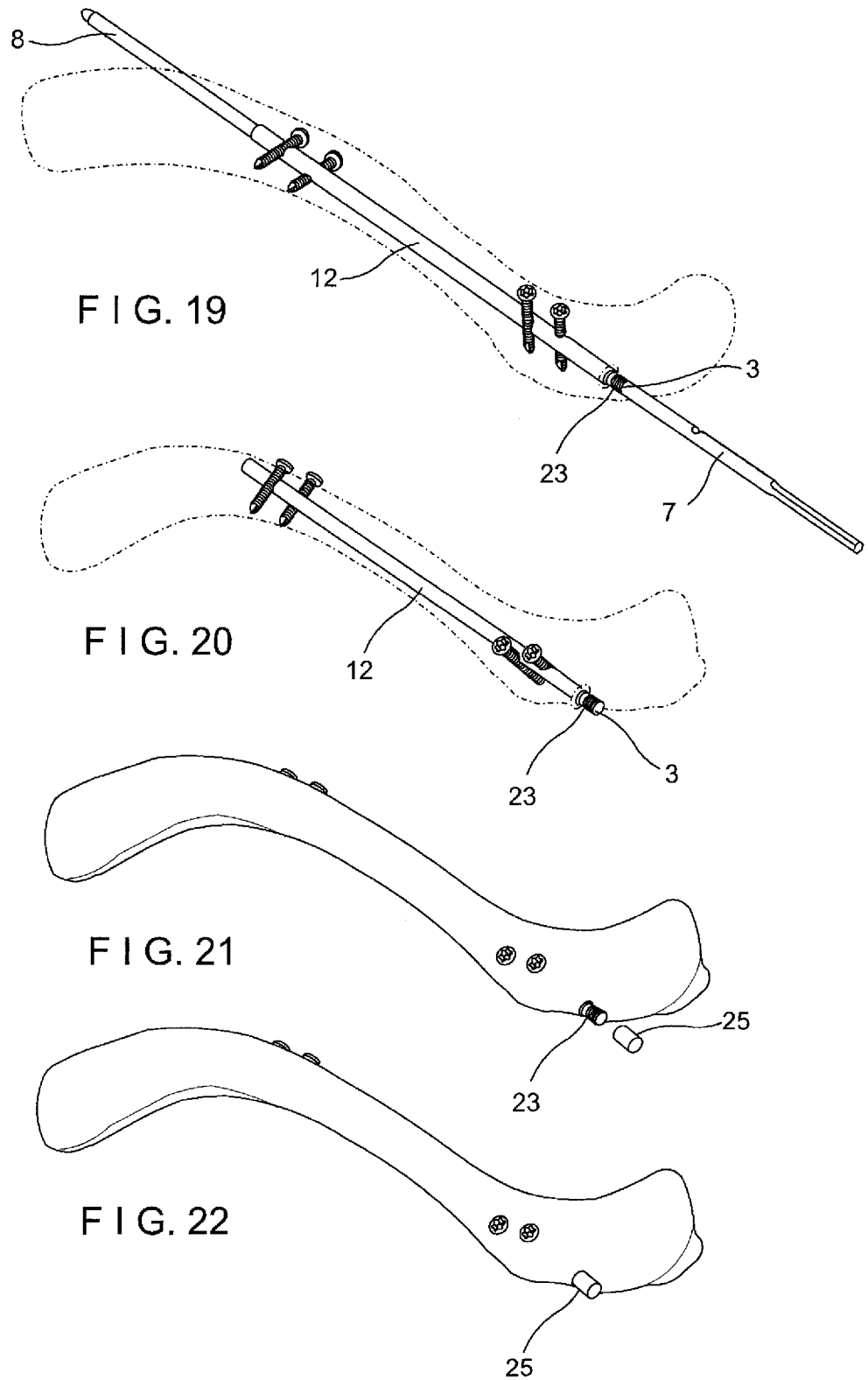
Figure 46:
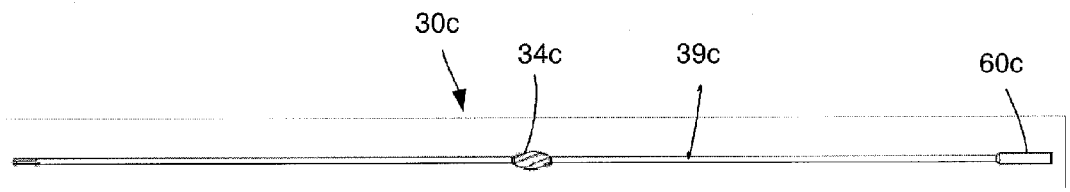
FIG. 46 illustrates a side view of a fourth embodiment of the reamer according to the invention.
Figure 47:
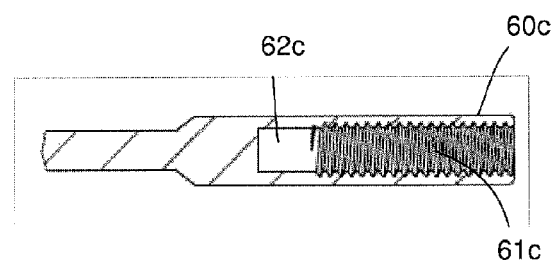
FIG. 47 illustrates an enlarged cross-sectional view of a proximal end of the reamer of FIG. 46.
Figure 48:
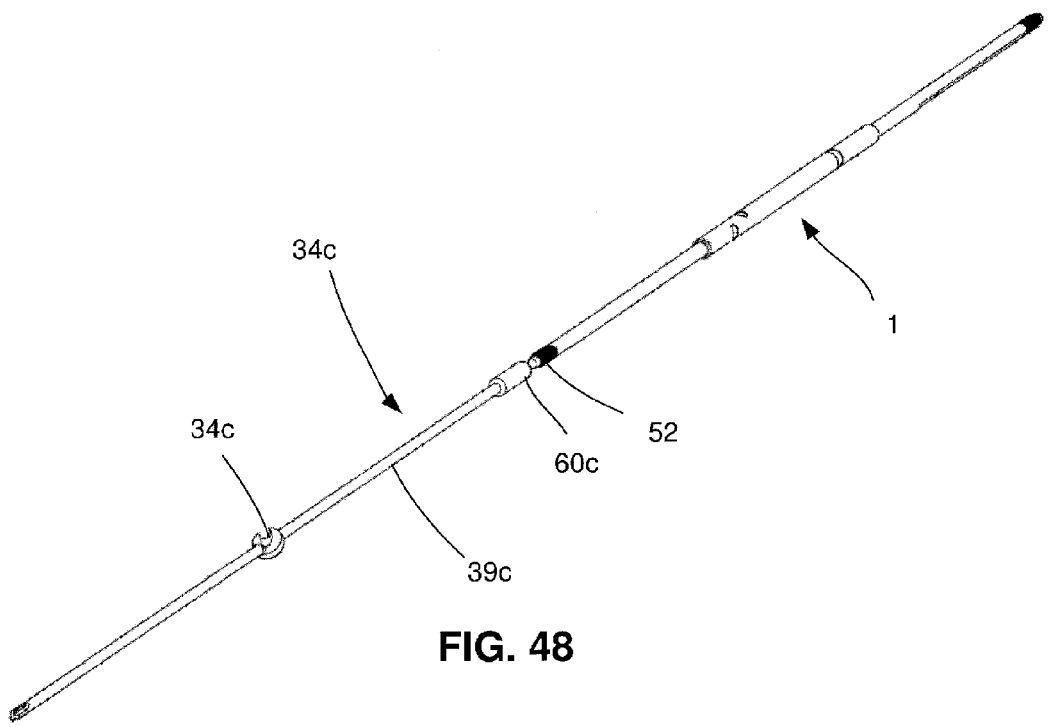
FIG. 48 illustrates a perspective view of the reamer of FIG. 46 coupled to a surgical nail according to the invention.

In a further embodiment, as shown in FIGS. 46-48, a reamer 30c may have a reamer head 34c. The reamer head 34c has the same features and properties as the reamer head 34. The reamer 30c has a proximal portion 39c that serves the same purpose as the proximal portion 39c. That is, the proximal portion 39c maintains the reduction of the bone fracture while the nail 1 is pulled into the clavicle 9. In this embodiment, the reamer head 34c is integrally formed with the proximal portion 39b. As shown in FIG. 47, a proximal end 60c includes a female thread 61c. The female thread 61c is formed within a recess 62c located in the proximal end 60c. As mentioned previously, and as shown in FIG. 48, the female thread can be coupled to a corresponding male thread provided on the distal end 52 so that the nail 1 may be pulled through the clavicle bone 9. As the skilled person would of course understand other means of coupling together the reamer 30c and the nail 1 are of course possible. For example, the reamer 30c and the nail 1 may be coupled via bayonet-type coupling or a press-fit coupling. FIG. 21 shows the reamer 104''' configured for pulling the nail 102 through a bone 10.

Although the reamer 30c is depicted as having only one reamer head, it will be understood by those of skill in the art that the reamer 30c may include any number of reamer heads. For example, the reamer 30c may include the reamer head configuration as described above in regard to the reamer 30b. It will be understood by those of skill in the art that any of the reamers 30, 30a, 30b and 30c may be utilized in the system of the present invention.

As shown in FIGS. 4-22, an exemplary embodiment of a surgical method for fixing a fractured clavicle involves insertion of the clavicle nail 1 of the first embodiment from a postero-lateral to an antero-medial direction of the clavicle 9. Although the following method describes a use of the nail 1, it will be understood by those of skill in the art that any of the nails 1a-1d, as described above, may be used in place of the nail 1. The method may comprise the steps of selecting a suitable clavicle nail 1 for a fractured clavicle 9 based, for example, on a length and diameter of the surgical nail 1 relative to the dimensions of the clavicle 9 as well as a distance between the proximal and distal locking apertures 5, 6. The fragmented portions of the clavicle 9 may be aligned and the reamer 30 may be used to drill the holes 32 through the clavicle 9 to accommodate the clavicle nail 1. The selected clavicle nail 1 may then be connected to the insertion handle 15, as shown in FIG. 4, so that the handle 15 facilitates insertion of the clavicle nail 1 into the fractured clavicle 9 through the hole 32 extending through the aligned bone fragments. It will be understood that two small skin-incisions may be necessary to permit the clavicle nail 1 to pass therethrough.

It will be understood by those of skilled in the art, that the reamer 30a may be used to form the hole 32 in a similar manner as described above in regard to reamer 30. Alternatively, the reamer 30b or 30c may be used to form the hole 32 in the clavicle 9. When the reamer 30b is used, the proximal portion 39b may remain within the clavicle 9 to maintain the reduction of the fracture, as shown in FIG. 45. As discussed above, the nail 1 may be slid over the proximal portion 39b or guided into the clavicle 9 via a pulling force on the proximal portion 39b. As described above, the nail 1 is formed so that it may flex as forces are exerted against it by the clavicle 9 as it is inserted along the bent path of the medullary canal during insertion and/or the hole 32. When the nail 1 has been inserted to its desired position within the clavicle 9, the proximal portion 39b is removed therefrom. As one of ordinary skill in the art would understand, a similar method may be used when the reamer 30c is used and coupled to the nail 1, as shown in FIG. 48.

The clavicle nail 1 is inserted into the clavicle 9 through the hole 32 until the distal portion 17 extends distally past the medial end 4 of the clavicle 9 such that the distal locking apertures 6 protrude from the medial end portion 10 of the clavicle 9, as shown in FIG. 5. The distal aiming arm 14 may then be slid over the distal rod 8 of such that the distal rod 8 extends through the central bore 43 of the sleeve 42, as shown in FIG. 6. The distal aiming arm 14 may be positioned so that an end of the sleeve 42 abuts the shoulder 18 at the transition between the distal rod 8 and the nail body 12. Once the distal aiming arm 14 has been appropriately positioned, the fixation screw 19 may be inserted through the lumen 46 such that the tip 40 of the fixation screw 40 passes through the transverse bore 47 and into the central bore 43, locking the distal aiming arm 14 relative to the clavicle nail 1, as shown in FIG. 7. Thus, the tip 40 of the fixation screw 19 extends into the notch 29 in the distal rod 8 of the surgical nail 1 such that the guide bores 21 of the distal aiming arm 14 are rotationally and axially aligned with the corresponding distal locking apertures 6 of the surgical nail 1. As shown in FIG. 8, a protection sleeve 20 may then be inserted into the guide bore 21 in the distal aiming arm 14 to verify that the bore axes 44 of the guide bores 21 in the distal aiming arm 14 are in alignment with the distal locking holes 6. A drill-bit 22 may be passed through the protection sleeve 20, as shown in FIG. 9, to confirm that the drill bit 22 extends along the central axes of the distal locking apertures 6. Once alignment has been verified, the protection sleeve 20 and the drill-bit 22 may be removed from the distal aiming arm 14.

As shown in FIGS. 10 and 11, the nail body 12 of the clavicle nail 1, along with the attached distal aiming arm 14, may then be moved toward the lateral end 11 of the clavicle 9 until the external thread 23 at the proximal end 3 of the nail body 12 protrudes from the lateral end 11 of the clavicle 9. The nail body 12 may be moved by pulling the insertion handle 15 proximally—i.e., toward the user. Once the nail body 12 has been positioned such that the threaded portion 23 is immediately proximal of the lateral end 11 of the clavicle 9, the handle 15 may be removed and the proximal aiming arm 13 may be slid over the proximal rod 7 of clavicle nail 1, as shown in FIG. 12, in the same manner as described above in regard to the distal aiming arm 14. The proximal aiming arm 13 may be locked relative to the nail 1 using a fixation screw 19, as shown in FIG. 13. As those skilled in the art will understand, the proximal aiming arm 13 may be coupled to the compression nut 70 prior to coupling the proximal aiming arm 13 to the proximal connecting element 28 so that the compression nut 70 is positioned between a proximal portion of the aiming arm 13 and the clavicle 9, as shown in FIG. 49, to compress the fracture.

Figure 16:
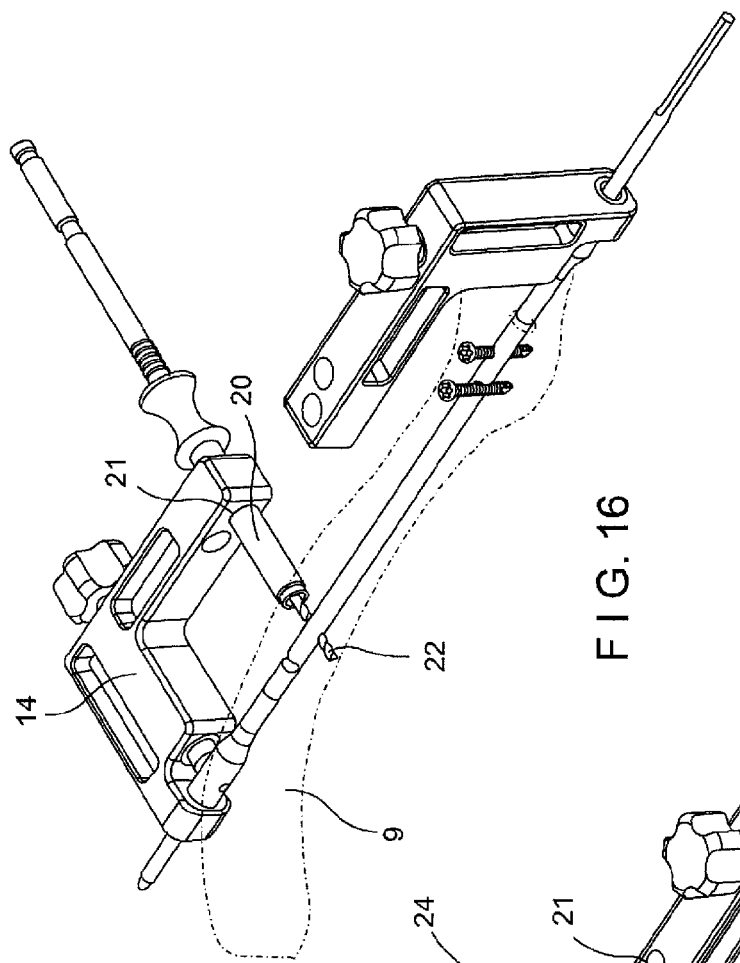
Figure 15:
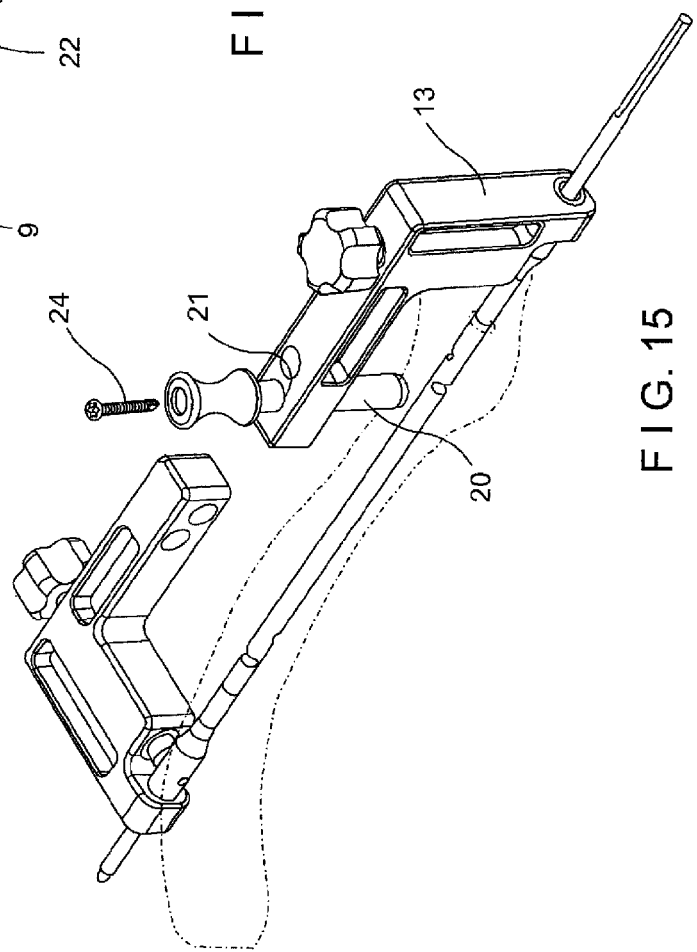

Once the clavicle 9 has been compressed, as desired, holes corresponding to the proximal locking apertures 5 may be drilled into the clavicle 9 by guiding a drill-bit 22 through a protection sleeve 20 that has been inserted into the respective guide bore 21 in the proximal aiming arm 13, as shown in FIG. 14. Proximal locking screws 24 may then be inserted through the protection sleeve 20, as shown in FIG. 15, and inserted into the respective guide bores 21 in the proximal aiming arm 13 to pass through the drilled holes in the clavicle 9 and into the proximal locking holes 5. The drill bit 22 may then be similarly used to drill distal holes via the guide bores 21 of the distal aiming arm 14 in the clavicle 9, as shown in FIG. 16, to correspond to the distal locking apertures 6 of the nail body 12. Distal locking screws 24 are then passed through the protection sleeve 20 extending through the respective guide bore 21 in the distal aiming arm 14 to pass through the drilled distal hole and into the corresponding distal locking aperture 6, as shown in FIGS. 17 and 18.

Once the locking screws 24 have been inserted into the bone to fix the nail body 12 relative to the clavicle 9, the proximal and distal aiming arms 13, 14 may be removed from the nail body 1 by removing the fixation screws 19. As shown in FIG. 19, although the nail body 12 is fixed relative to the clavicle 9, thereby fixing the fracture thereof, the distal and proximal rods 8, 7 remain extending from the lateral and medial 11, 10 ends of the clavicle 9. Thus, as shown in FIG. 20, a portion of the distal rod 8 extending distally from the lateral end 11 of the clavicle 9 is cut off at the bone interface. Similarly, a portion of the proximal rod 7 extending proximally from the medial end 19 of the clavicle 9 is cut from a remaining portion there immediately proximally of the external thread 23 of the nail body 12. An end cap 25, as shown in FIGS. 21 and 22, may be placed over the external thread 23 of the nail body 12 to protect the proximal end 3 of the nail body 12 from bone ingrowth. The medial and lateral incisions in the patient's body are then closed. It will be understood by those of skill in the art that where the clavicle nail is the nail 1c, the proximal and/or distal rods 7, 8 extending from the clavicle 9 may be cut along the grooves 109.

Another exemplary embodiment of a surgical method for fixing a fractured clavicle involves insertion of the clavicle nail 1a of the second embodiment into the clavicle 9. The method is substantially as described for the first embodiment with the exception that the removably coupled distal and proximal portions 8a, 7a are not cut but removed from the coupling arrangement with, for example, a tool (not shown) from their respective connection with the nail body 12a. That is, the tool is used remove the distal and proximal portions 8a, 7a for the press-fitted coupling arrangement, for example.

In yet another exemplary embodiment of a surgical method, where the clavicle nail is the nail 1b of the third embodiment, the method is as described for the first embodiment for the distal connecting element 27b and as described for the second embodiment for the proximal connecting element 28b. That is, the proximal connecting element 28b is cut after the nail 1b has been positioned in the clavicle and is then covered with the endcap 25 to cover any sharp edges and minimize the potential for soft tissue irritation. The removably coupled distal connecting element 27b is then removed from its coupling arrangement with the nail body 12b by, for example, a tool (not shown).

In another exemplary embodiment of a surgical method utilizing the nail 1e, the method may be substantially similar to the method described above in regard to the nail 1. Since the nail 1e only includes a distal connecting element 8e, however, only the distal aiming arm 14 will be attached to the distal connecting element 8e to guide a drill tool and/or distal locking screws through the distal apertures 6e. A proximal locking screw may be inserted through the proximal locking aperture 5e via a proximal opening of the hole 32 in the clavicle 9.

Figure 23:
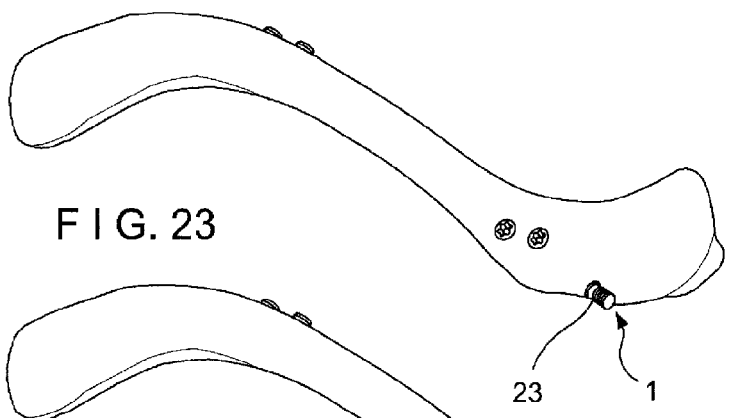
FIG. 23-26 illustrate a perspective view of the removal of the surgical nail according to the invention.
Figure 24:
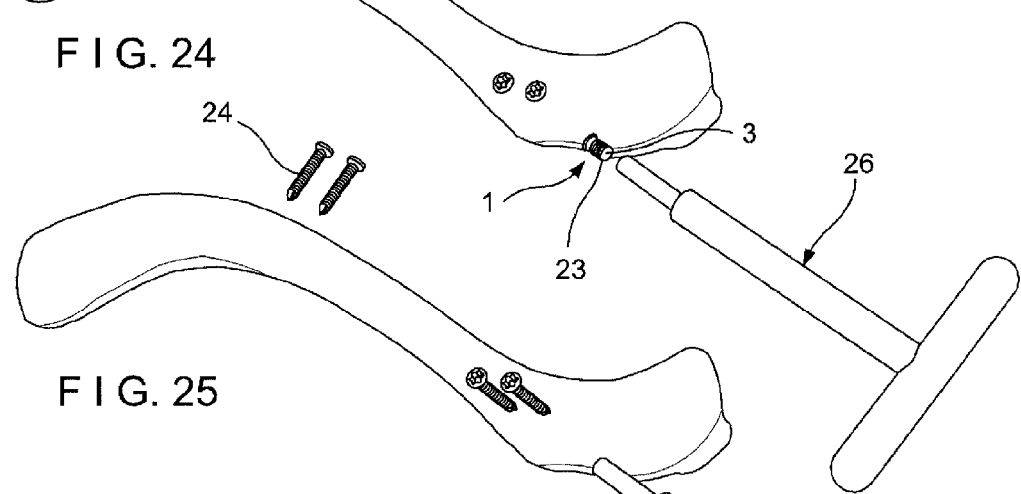
Figure 25:
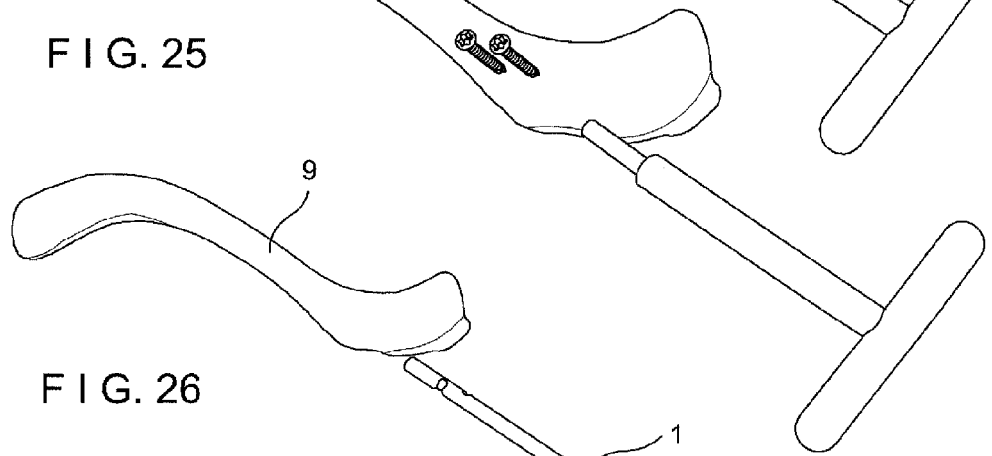
Figure 26:
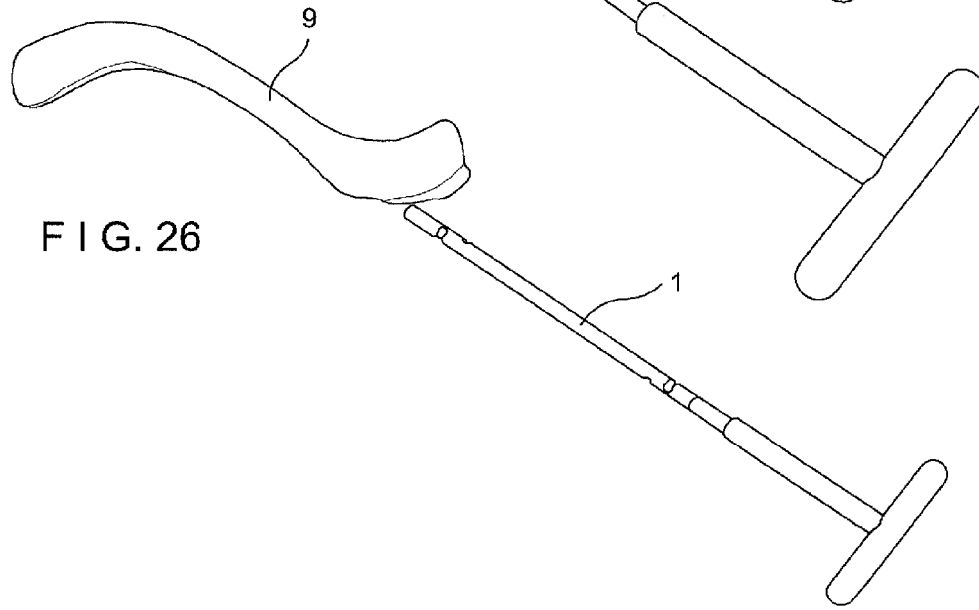

As shown in FIGS. 23-26, a method according to another exemplary embodiment of the present invention includes removal of the clavicle nail 1 from the clavicle 9, if desired. The clavicle nail 1 may be removed from the clavicle 9 by removing the end cap 25 by unthreading the end cap 25 from the threaded portion 23 at the proximal end 3 of the nail body 12, as shown in FIG. 23. A removal instrument 26, as shown in FIG. 24, may then be coupled to the external thread 23 at the proximal end 3 of the nail body 12 to provide a gripping handle for a user. It should be noted that the locking screws 24 should remain in place to prevent the clavicle nail 1 from rotation during attachment of the removal instrument 26. Once the removal instrument 26 has been coupled to the nail body 12, the locking screws 24 may be removed from the clavicle 9, as shown in FIG. 25. Once all the locking screws 24 have been removed, the user may, for example, draw the removal handle 26 proximally to pull the clavicle nail 1 from the clavicle 9, as shown in FIG. 26.

Although the exemplary method, as described above, describes insertion of the clavicle nail 1 from a postero-lateral to an antero-medial direction of the clavicle 9, it will be understood by those of skill in the art that the clavicle nail 1 may also be inserted into a clavicle 9 form antero-medial to postero-lateral. According to an alternate embodiment of the present invention, the clavicle nail 1 is inserted into the clavicle 9 with the proximal end 3 of the nail body 12 located at the medial end portion 10 of the clavicle 9 and with the distal end 4 of the nail body 12 located at the lateral end portion 11 of the clavicle 9. As will be understood by those skilled in the art this embodiment of the surgical method is substantially similar to the exemplary method described above. The method for fixation of a fractured clavicle by inserting a clavicle nail from antero-medial to postero-lateral may be performed by using the same clavicle nail 1 and the same instruments, as discussed above. The same proximal and distal aiming arm 13, 14 may also be used. The clavicle nail 1, however, should be rotated about its longitudinal axis 2 approximately 90° so that the central axes 38 of the proximal locking apertures 5 extend in an antero-posterior direction and the central axes 38 of the distal locking apertures 6 extend in a sagittal direction. As would be understood by those of skill in the art, the clavicle nail 1 is inserted from the medial end 10 to the lateral end 11 of the clavicle 9 until the distal portion 17 of the nail 1, comprising the distal locking apertures 6, protrudes distally from the lateral end portion 11 of the clavicle 9. Similarly, once alignment of the guide bore 21 and the distal locking apertures 6 have been verified, as described above, the nail body 12 of the clavicle nail 1, with the distal aiming arm 14 attached, is moved medially into the clavicle 9 until the external thread 23 at the proximal end 3 of the nail body 12 protrudes from the medial end portion 10 of the clavicle 9. The nail body 12 may be moved accordingly by, for example, pulling the insertion handle 15 attached to the proximal end 51 of the nail 1.

Although the invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art.

What is claimed is:

1. A surgical nail for treating a bone, comprising:
   a nail body extending along a longitudinal axis from a first end to a second end and including a first locking aperture extending transversely through a first end portion thereof and a second locking aperture extending transversely through a second end portion thereof, the nail body having an initial undeformed configuration and a flexibility selected so that the nail body is deformable during insertion into the bone, the nail body returning toward the initial undeformed configuration upon the nail body reaching a desired final position; and
   a first connecting element coupled to a second end of the nail body, the first connecting element extending from the second end of the nail body by a length $L_X$ selected so that, when the nail body is implanted to a desired position within the bone, at least a portion of the first connecting element projects out of the bone so that it is available for coupling to a first aiming guide external to the bone.

2. The surgical nail according to claim 1, wherein the first connecting element is a rod extending away from a second end of the nail body substantially coaxially with the longitudinal axis thereof.

3. The surgical nail according to claim 1, wherein the angle at which the second locking aperture extends is offset with respect to the first locking aperture.

4. The surgical nail according to claim 1, wherein the second locking aperture and the first locking aperture extend substantially along the same plane relative to each other.

5. The surgical nail according to claim 1, wherein, in an undeformed state, the nail body is substantially straight.

6. The surgical nail according to claim 1, wherein, in an undeformed state, the nail body is curved.

7. The surgical nail according to claim 1, wherein the nail body comprises a substantially triangular cross-section.

8. The surgical nail according to claim 1, wherein the nail body comprises a substantially flattened cross-section.

9. The surgical nail according to claim 8, wherein the area of the nail body comprising the flattened cross-section is helical in shape.

10. The surgical nail according to claim 1, wherein one of the first and second locking apertures are U-shaped grooves offset from the longitudinal axis of the nail body and open to an exterior of the nail body.

11. The surgical nail according to claim 1, wherein the initial undeformed configuration has a curvature corresponding to a curvature of a portion of the bone through which the nail is to be inserted.

12. The surgical nail according to claim 1, wherein a portion of the nail body has a reduced diameter portion.

13. The surgical nail according to claim 12, wherein the portion is overmolded with a viscoelastic polymer.

14. The surgical nail according to claim 1, wherein the first locking aperture extends from the first end of the nail body through a wall thereof such that an axis of the first locking aperture extends at an angle with respect to the longitudinal axis.

15. A surgical nail for treating a bone, comprising:
   a nail body extending along a longitudinal axis from a first end to a second end and including a first locking aperture extending transversely through a first end portion thereof and a second locking aperture extending transversely through a second end portion thereof;
   a first connecting element coupled to a second end of the nail body, the first connecting element extending from the second end of the nail body by a length $L_X$ selected so that, when the nail body is implanted to a desired position within the bone, at least a portion of the first connecting element projects out of the bone so that it is available for coupling to a first aiming guide external to the bone; and a second connecting element coupled to the first end of the nail body, the second connecting element extending from the first end of the nail body by a length $L_C$ selected so that, when the nail body is implanted to a desired position within the bone, at least a portion of the second connecting element projects out of the bone so that it is available for coupling to a second aiming guide external to the bone.

16. The surgical nail according to claim 15, wherein the second connecting element is a rod extending away from the first end substantially coaxially with the longitudinal axis of the nail body.

17. The surgical nail according to claim 15, wherein the first and second connecting elements have a cross-sectional area no larger than a cross-sectional area of the nail body, wherein the nail body has a maximum diameter D and the first and second rods have a maximum diameter d<D.

18. The surgical nail according to claim 15, wherein the second end portion of the nail body has a length $L_D$ extending from the second end of the nail body and the second connecting element extends from the first end of the nail body over a length $L_C$ which is no less than $L_D$.

19. The surgical nail according to claim 18, wherein the ratio of $L_C$ to $L_D$ has a minimum value of 1.0.

20. The surgical nail according to claim 18, wherein the ratio of $L_C$ to $L_D$ has a minimum value of 3.0.

21. The surgical nail according to claim 15, wherein one of the first connecting element and the second connecting element is removably coupled to the nail body.

22. A surgical nail for treating a bone, comprising:
a nail body extending along a longitudinal axis from a first end to a second end and including a first locking aperture extending transversely through a first end portion thereof and a second locking aperture extending transversely through a second end portion thereof;
a first connecting element coupled to a second end of the nail body, the first connecting element adapted and configured to be coupled to a first aiming guide; and
a second connecting element coupled to the first end of the nail body, the second connecting element adapted and configured to be coupled to a second aiming guide wherein each of the first and second connecting elements includes a through bore extending transversely therethrough along a corresponding bore axis, the bore axis of the through bore extending through the second connecting element being substantially parallel to a central axis of the first locking aperture and the bore axis of the through bore extending through the second locking element being substantially parallel to the central axis of the second locking aperture.

* * * * *